(12) United States Patent
Zhe et al.

(10) Patent No.: US 8,522,604 B2
(45) Date of Patent: Sep. 3, 2013

(54) METAL WEAR DETECTION APPARATUS AND METHOD EMPLOYING MICROFLUIDIC ELECTRONIC DEVICE

(75) Inventors: Jiang Zhe, Copley, OH (US); Li Du, Akron, OH (US); Joan E. Carletta, Broadview Heights, OH (US); Robert J. Veillette, Akron, OH (US)

(73) Assignee: The University of Akron, Akron, OH (US)

( * ) Notice: Subject to any disclaimer, the term of this patent is extended or adjusted under 35 U.S.C. 154(b) by 833 days.

(21) Appl. No.: 12/609,125

(22) Filed: Oct. 30, 2009

(65) Prior Publication Data
US 2010/0109686 A1 May 6, 2010

Related U.S. Application Data

(60) Provisional application No. 61/110,208, filed on Oct. 31, 2008.

(51) Int. Cl.
*G01N 27/74* (2006.01)

(52) U.S. Cl.
USPC ......... 73/61.71; 73/53.05; 73/53.07; 324/204

(58) Field of Classification Search
USPC .................. 73/53.05, 53.07, 61.71; 422/502, 422/503; 336/20
See application file for complete search history.

(56) References Cited

U.S. PATENT DOCUMENTS

| | | | | |
|---|---|---|---|---|
| 2,656,508 A | * | 10/1953 | Coulter | 324/71.1 |
| 5,001,424 A | * | 3/1991 | Kellett et al. | 324/204 |
| 5,041,856 A | * | 8/1991 | Veronesi et al. | 324/204 |
| 5,262,732 A | | 11/1993 | Dickert et al. | |
| 5,485,083 A | | 1/1996 | Pulice | |
| 5,519,317 A | | 5/1996 | Guichard et al. | |
| 5,604,441 A | | 2/1997 | Freese et al. | |
| 5,668,309 A | * | 9/1997 | Codina et al. | 73/61.71 |
| 5,767,672 A | | 6/1998 | Guichard et al. | |
| 5,811,664 A | * | 9/1998 | Whittington et al. | 73/53.07 |
| 6,191,580 B1 | | 2/2001 | Guichard | |
| 6,204,656 B1 | * | 3/2001 | Cheiky-Zelina et al. | 324/71.4 |
| 6,424,145 B1 | | 7/2002 | Woolsey et al. | |
| 7,397,232 B2 | * | 7/2008 | Hu et al. | 324/71.4 |
| 7,541,004 B2 | * | 6/2009 | Niksa et al. | 422/82.02 |
| 7,611,673 B2 | * | 11/2009 | Kartalov et al. | 422/502 |
| 7,777,476 B2 | * | 8/2010 | Hu et al. | 324/71.4 |

(Continued)

FOREIGN PATENT DOCUMENTS
WO WO 01/18246 3/2001

OTHER PUBLICATIONS

Holzhaauer W., Murray S. F., 1983, Continuous wear measurement by on-line ferrography, Wear, 90, pp. 11-19.*

(Continued)

*Primary Examiner* — Leonard Chang
*Assistant Examiner* — Natalie Huls
(74) *Attorney, Agent, or Firm* — Renner Kenner Greive Bobak Taylor & Weber

(57) ABSTRACT

An apparatus and a method for detection of wear particles in a lubricant are disclosed. The apparatus includes a microfluidic device including a microchannel sized for a lubricant containing wear particles to pass therethrough and first and second electrodes extending into the microchannel. A detection system is coupled with the electrodes for detection of wear particles passing through the microchannel, based on a change in capacitance of the electrodes.

27 Claims, 25 Drawing Sheets

(56) References Cited

U.S. PATENT DOCUMENTS

| | | | |
|---|---|---|---|
| 7,784,332 B2* | 8/2010 | Cho et al. | 73/61.71 |
| 7,956,601 B2* | 6/2011 | Becker et al. | 324/204 |
| 8,354,836 B2* | 1/2013 | Becker et al. | 324/204 |
| 2006/0105467 A1* | 5/2006 | Niksa et al. | 436/150 |
| 2008/0087076 A1* | 4/2008 | Busch | 73/61.71 |
| 2008/0150518 A1* | 6/2008 | Becker et al. | 324/204 |
| 2010/0089131 A1* | 4/2010 | Niksa et al. | 73/53.05 |
| 2010/0319437 A1* | 12/2010 | Cho et al. | 73/61.71 |

OTHER PUBLICATIONS

Sohn L.L., Saleh O.A., Facer G.R., Beavis A.J and Allan R.S, 2000, Capacitance cytometry: measuring biological cells one by one, Proceedings of the National Academy of Sciences, 97, pp. 10687-10690.*

Brown J.R., 1980, *Particle size independent spectrometric determination of wear metals in aircraft lubricating oils*, Analytical Chemistry, 52, pp. 2365-2370.

Centers P.W., 1990, Oil monitoring technology, AUTOTESTCON '90; IEEE Systems Readiness Technology Conference, San Antonio, TX, United States, pp. 523-528.

Chambers K.W., 1988, An online ferromagnetic wear debris for machinery condition and fault detection, Wear, 128, pp. 325-337.

Charlton B., Fisher A.S., Goodall P.S., Hinds M.W., Lancaster S. and Salisbury M., 2007, Atomic spectrometry update: Industrial analysis: metals, chemicals and advanced materials, Journal of Analytical Atomic Spectrometry, 22, pp. 1497-1528.

Edmonds J., Resner M.S. and Shkarlet K., 2000, Detection of precursor wear debris in lubrication systems, Aerospace Conference Proceedings, IEEE , 6, pp. 73-77.

Flanagan I. M., Jordan J.R. And Whittington H.W., 1990,An inductive method for estimating the composition and size of metal particle, Measurement Science and Technology, 1, pp. 381-384.

Flanagan I. M., Jordan J. R. and Whittington H. W., 1988, Wear-debris detection and analysis techniques for lubricant-based condition monitoring. Journal of Physics E: Scientific Instruments., 21, pp. 1011-1016.

Henriquez R., et al. The Resurgence of Coulter Counting for Analyzing Nanoscale Objects, *The Royal Society of Chemistry*, 2004.

Irvine Sensors Corporation, MS3110 Universal Capacitance Readout IC datasheet.

Jagtiani A., et al. *A label-free high throughput resistive-pulse sensor for simultaneous differentiation and measurement of multiple particle-laden analytes*, Jun. 26, 2006.

Keller M. and Saba C., 1989, Monitoring of ester based lubricant by dielectric constant, Transactions of Society of Tribologists and Lubrication Engineers, 45 (6), pp. 347-351.

Khandaker G., Glavas E. and Jones G. R., 1993, A fibre-optic oil condition monitor based on chromatic modulation, Measurement Science and Technology, 4, pp. 608-613.

Liu Y., Liu Z., Xie Y. and Yao Z., 2000, Research on an on-line wear condition monitoring system for marine diesel engine, Tribology International, 33, pp. 829-835.

Miller J. L., Kitaljevich D., 2000, In-line oil debris monitor for aircraft engine condition assessment, Aerospace Conference Proceedings, Big Sky, MT, USA, pp. 49-56.

Murali S., et al. *A Microfluidic Coulter Counting Device for Metal Wear Detection in Lubrication Oil*, American Institute of Physics, 2009.

Murali S. *Capacitive Coulter Counting: Detection of Metal Wear Particles in Lubricant Using a Microfluidic Device*, Smart Mater. Struct. 18, 2009.

Raadnui S. and Kleesuwan S., 2005, Low cost condition monitoring for used oil analysis, Wear, 259, pp. 1502-1506.

Sohn L.L., Saleh O.A., Facer G.R., Beavis A.J and Allan R.S, 2000, Capacitance cytometry: measuring biological cells one by one. Proceedings of the National Academy of Sciences, 97, pp. 10687-10690.

Zhang J. et al., An electronic pollen detection method using Coulter counting principle, Atmospheric Environment 39, 2005, pp. 5446-5453.

Zhe J., Jagtiani, A.V. Dutta P., Hu J. and Carletta J , 2007, A micromachined high throughput Coulter counter for bioparticle detection and counting. Journal of Micromechanics and Microengineering, 17, pp. 304-313.

Howe, B. and Muir, D. 1998, In-line oil debris monitor (ODM) for helicopter gearbox condition assessment, DTIC, AD-a, 374, pp. 503-508.

Irvine Sensors Corporation, MS3110 Universal Capacitance Readout IC datasheet, 2001.

* cited by examiner

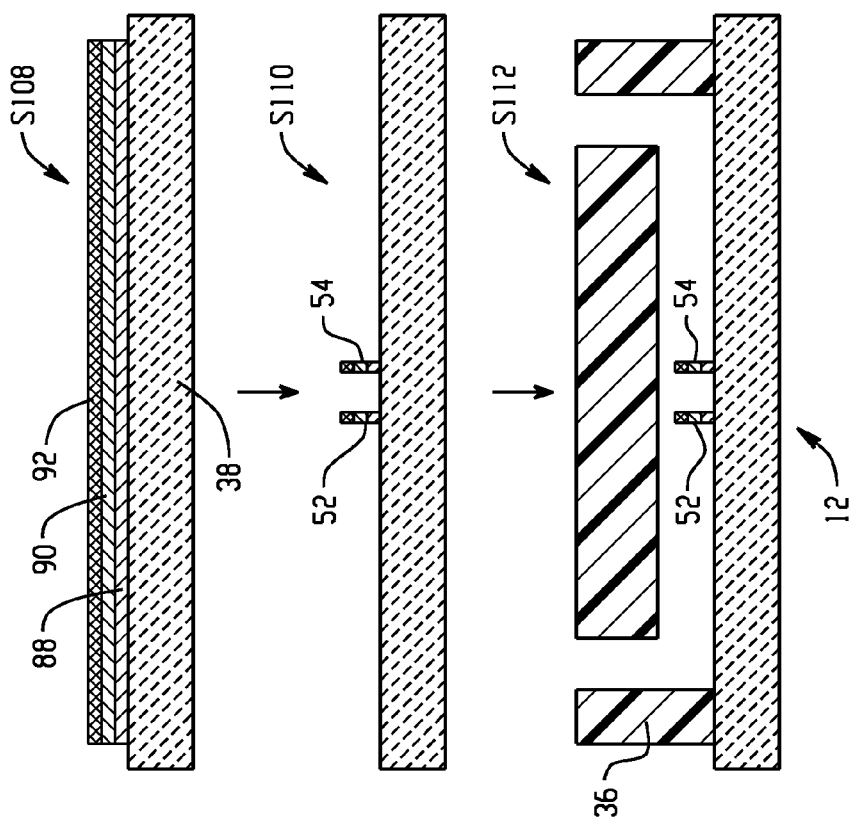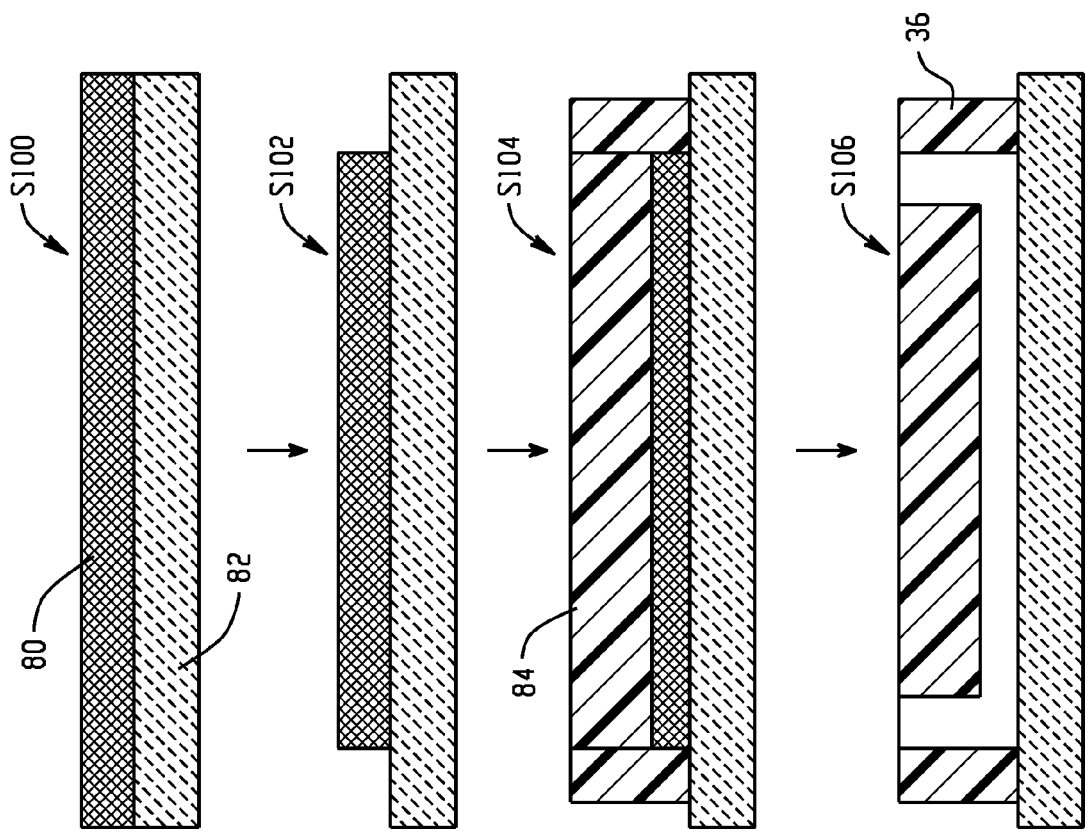
Fig. 4

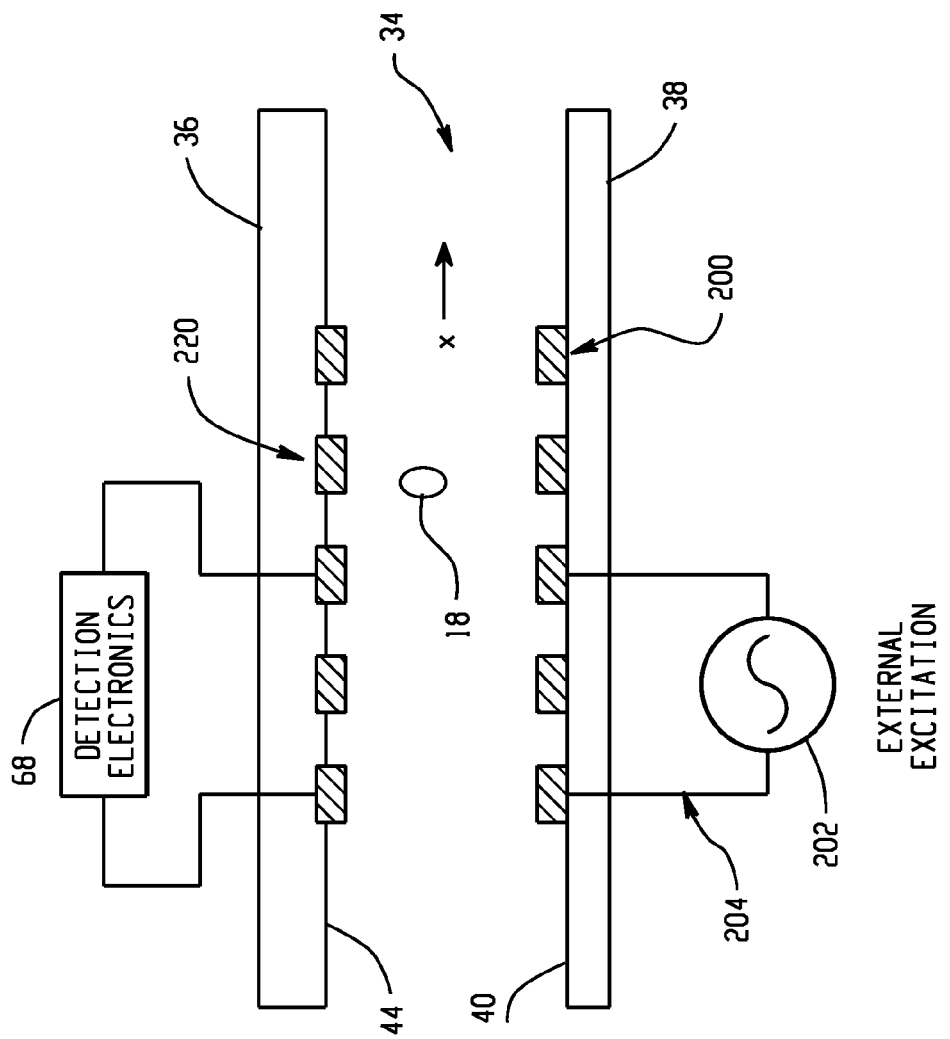

METAL WEAR DETECTION APPARATUS AND METHOD EMPLOYING MICROFLUIDIC ELECTRONIC DEVICE

This application claims the benefit of U.S. Provisional Application Ser. No. 61/110,208, filed Oct. 31, 2008, the disclosure of which is incorporated herein in its entirety by reference.

BACKGROUND

The exemplary embodiment relates to the detection of wear particles in a lubrication fluid, such as oil. It finds particular application in connection with a microfluidic device for detecting or measuring an electrical property of the lubrication fluid which changes as the fluid becomes contaminated with wear particles.

Machine parts, such as aircraft engines and gear boxes in which components move relative to each other, are often lubricated with a lubricant oil to reduce wear. However, over time, small wear particles with sizes in the range of 1-10 microns (μm) are generated. When abnormal wear begins, larger particles, in the range of 10 to 50 microns are generated. The particle population and size of the particles tends to increase over time until eventually, a machine failure can result.

To monitor the change in lubricant wear particles, samples of the oil may be withdrawn from the machine at scheduled times and sent to a laboratory for analysis. A variety of off-line methods exist for measuring properties of lubricating fluids. For example, the suspended particles may be separated from the oil sample, e.g., by using a rotary particle depositor, and the amount of particulate matter contained in a given sample volume of oil is then quantified. Another method involves placing the sample in a container and creating a magnetic flux field using a sensing electromagnetic coil. The distortion of the flux field caused by the particle burden is then noted as a numerical Particle Quantifying (PQ) value (see U.S. Pat. No. 5,404,100). However, each of these methods takes time to generate wear information. As a result, critical failures of machines may occur even when samples are sent regularly for testing.

Ferrography is another method for lubricant debris analysis. However, the test procedure is very lengthy, and requires complicated setup and a skilled analyst (See, Roylance B. J., 2005, *Tribology International*, v. 38, pp. 857-862). Optical methods such as scattering counters are capable of detecting particles in oil. However, the accuracy of the optical approach is affected by particle properties (refractive index, shape, etc) and the existence of air bubbles, and is effective only for debris larger than 50 μm (See Khandakar G. and Jones G. R., 1993, *Meas. Sci. Tech.*, v. 4, pp. 608). Magnetic inductive debris sensors have met some success but are limited to ferromagnetic debris larger than 100 μm (See, Campbell. P., 1991, *Int. Condition Monitoring Conf. Proc.*, pp. 325-335). For example, U.S. Pat. No. 5,604,441 discloses a method and apparatus for detecting the degree of deterioration of a lubricating oil for an operating machine which includes a grid-like capacitive sensor that uses the lubricating oil as a dielectric medium. A magnetic field is imposed upon the oil to attract ferromagnetic wear particles into the vicinity of the sensor. Capacitance measurements are taken at periodic intervals at each of several magnet operational states for respective classification and analysis. The magnets are simultaneously de-energized for release of captured particles back in to an oil circulation stream and to clean the capacitative sensor grid of accumulated particulates. Such a method, however, is only applicable to ferromagnetic particles present in relatively high concentrations.

There remains a need for a method which permits in-situ testing of lubricants that allows a rapid response when wear particles reach a critical size or number and which is applicable to wear particles that do not have ferromagnetic properties.

BRIEF DESCRIPTION

In accordance with one aspect of the exemplary embodiment, an apparatus for detection of wear particles in a lubricant includes a microfluidic device and a detection system. The microfluidic device includes a microchannel sized for a lubricant containing wear particles to pass therethrough and one or more electrodes extending into the microchannel. The detection system is coupled with the electrode(s) for detection of wear particles passing through the microchannel based on a change in an electrical property, such as capacitance or inductance, of the electrode(s).

In another aspect, a method for detection of wear particles in a lubricant includes supplying a lubricant containing wear particles to a microchannel. Changes in an electrical property, such as capacitance of electrodes or inductance in a coil positioned in the microchannel are monitored. Wear particles passing through the microchannel are detected, based on a change in the electrical property.

In another aspect, a method for forming an apparatus for detection of wear particles in a lubricant includes forming first and second electrodes or a coil on a substrate and mounting a body to the substrate such that a microchannel is defined over the electrodes/coil between the substrate and the body. The method further includes coupling the electrodes/coil ends with a detection system capable of detecting a change in an electrical property when a lubricant containing a wear particle passes through the microchannel.

In another aspect, an apparatus for detection of wear particles in a lubricant includes a microfluidic device comprising a microchannel sized for a lubricant containing wear particles to pass therethrough, the microchannel being sized such that particles are predominantly detected singly as they pass through the microchannel, and first and second electrodes extending into the microchannel. A detection system is coupled with the electrodes for detection of a wear particle passing through the microchannel based on a change in at least one of capacitance and inductance of the electrodes.

BRIEF DESCRIPTION OF THE DRAWINGS

FIG. 4 illustrates a method of forming the microfluidic device;

FIG. 13 is a schematic side view of a microchannel of a microfluidic device in accordance with another aspect of the exemplary embodiment with a coiled electrode and separate detection circuit which may be used for inductance measurements in an apparatus analogous to that of FIG. 1;

FIG. 25 shows the baseline voltage across an oil-filled solenoid (a) with no particle, FIG. 26 shows the voltage with 1 mm, 2 mm, and 2.84 mm chromium steel particles, respectively, and FIG. 27 shows the voltage with 1.98 mm, 2.34 mm, and 3.18 mm aluminum particles, respectively.

DETAILED DESCRIPTION

To address the problem of detection of wear particles, the exemplary embodiment utilizes a Coulter counting principle to detect and count metal wear particles generated in a lubricant, such as an oil. The wear particles need not have magnetic properties, for example, the wear particles may be formed from non-ferrous metals, such as aluminum or other non-magnetic material. While some of the wear particles detected may be formed of ferrous materials, such as iron or steel, in the exemplary embodiment, at least some of the particles may be predominantly formed (i.e., at least 50% by weight) of non-ferrous metals. Two detection methods are discussed, one based on capacitance, the other based on inductance.

1. Capacitance Measuring Device

An exemplary microflidic device includes two reservoirs connected by a microfluidic channel (a "microchannel"). When a particle is present in the microchannel, it causes a change in resistance of the lubricant-filled microchannel. Because lubricant oil is non-conductive, the resistance change due to the passage of a particle is difficult to measure. To overcome this, the change in capacitance formed between two electrodes in the microchannel is monitored. When a metal particle passes through the microchannel, a change in the capacitance can be detected due to the difference in permittivity between the lubricant oil and the metal particle. In one embodiment, a multichannel device having many microfluidic channels can be used to improve the detection throughput significantly.

Figure 1:
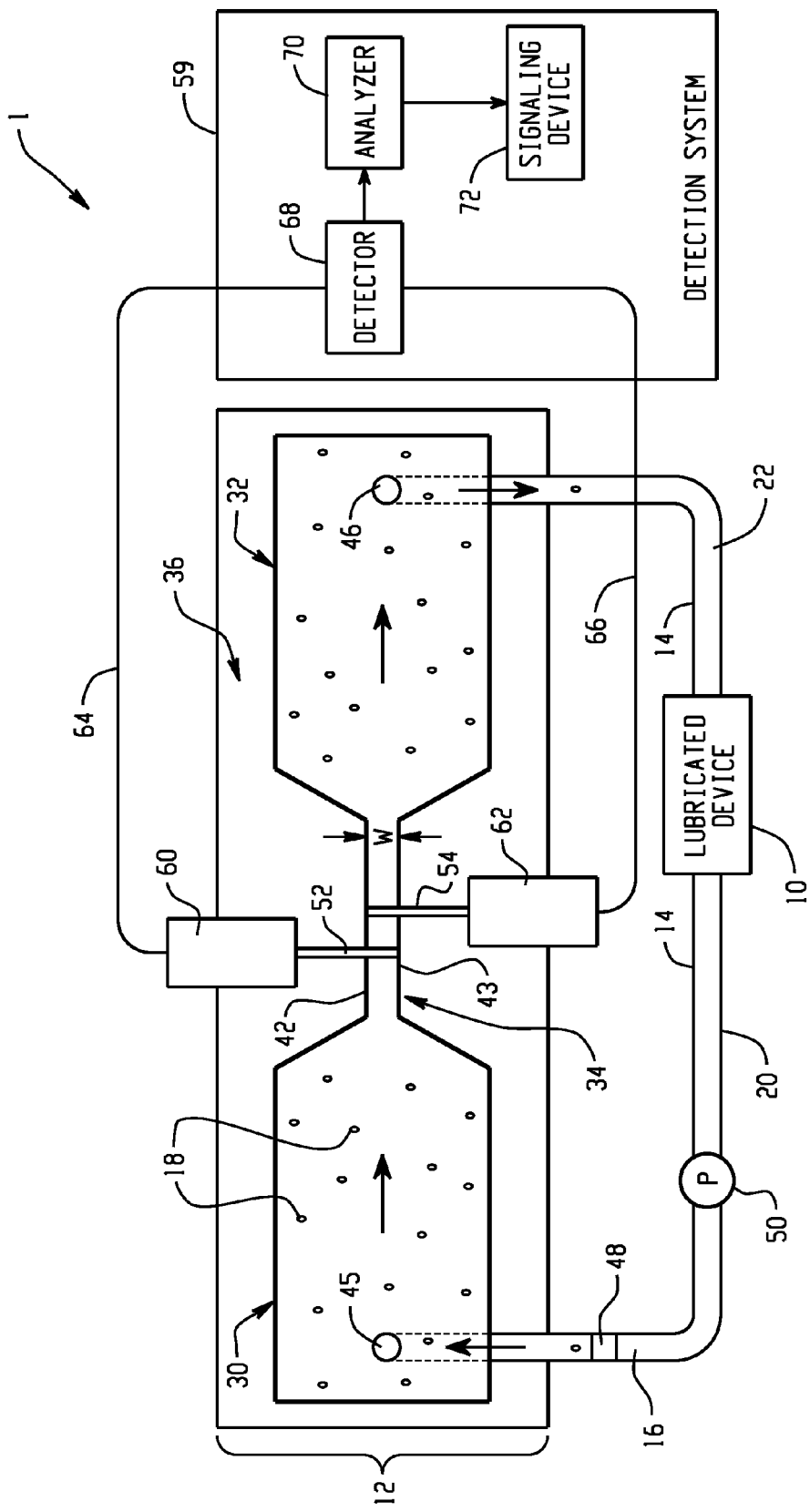
FIG. 1 is a schematic top view of a wear detection apparatus employing a microfluidic device in accordance with one aspect of the exemplary embodiment.

With reference to FIG. 1, an apparatus 1 for detection of wear particles in a lubricant is shown. The apparatus 1 may receive lubricant from an associated device 10. The lubricated device 10 may be a motor or gear box and contains a lubricant, such as motor oil, for lubricating component parts. During operation, wear particles are generated from these components and are circulated throughout the lubricant.

The apparatus 1 includes a microfluidic device 12. The microfluidic device 12 is capable of detection of microscale debris, such as particles in the range of 10-100 µm in a liquid, such as lubricant oil. Microfluidic device 12 receives lubricant 16 containing wear particles 18 from the lubricated device 10. Device 12 may be in communication with lubricated device 10 via a fluid pathway 14, as shown in FIG. 1. In the illustrated embodiment, the lubricated device 10 is connected with the microfluidic device 12 by an inlet tube 20 and a return tube 22, although in other embodiments, the return tube may be connected with a waste line.

Figure 2:
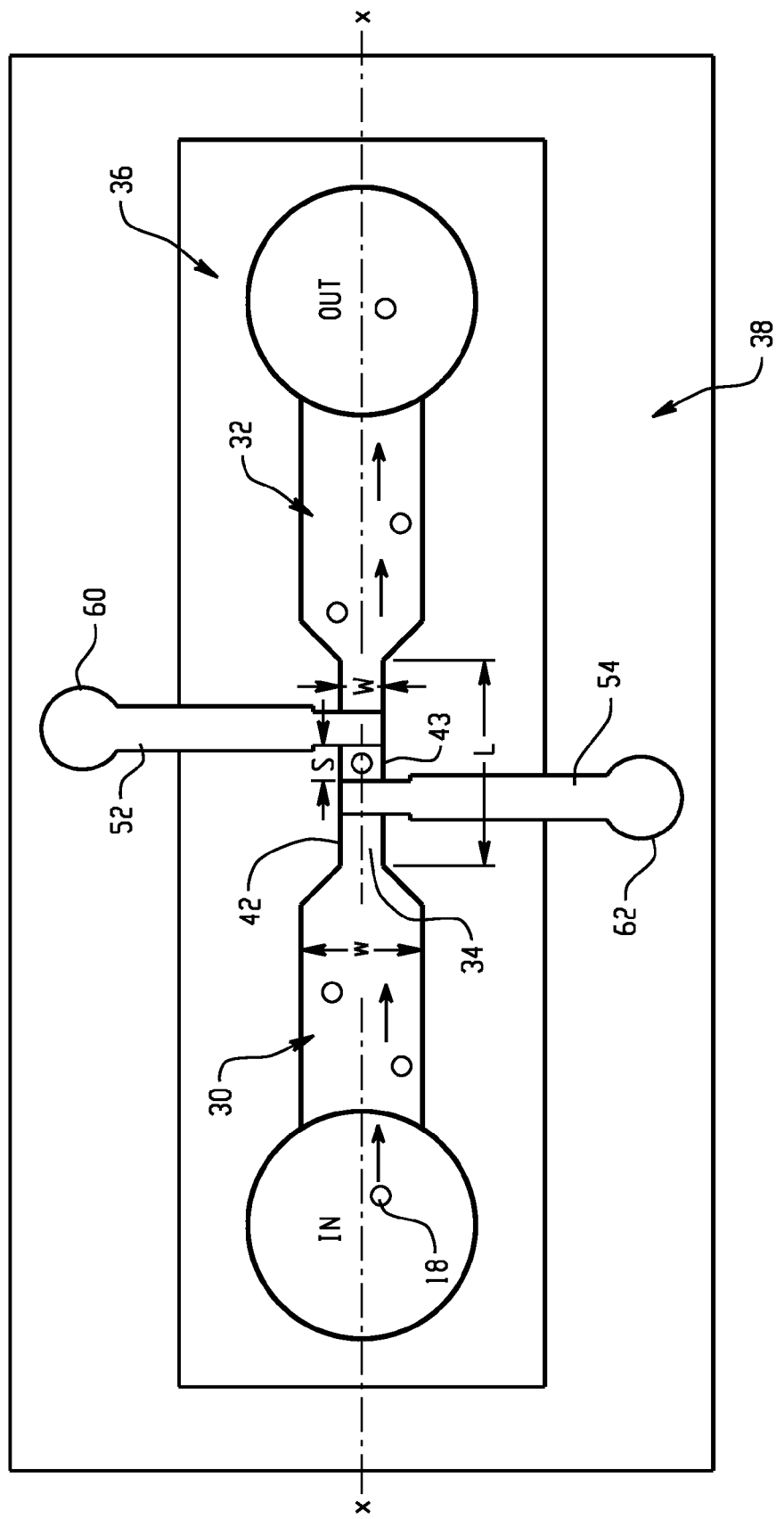
FIG. 2 is a top plan view of the microfluidic device of FIG. 1.
Figure 3:
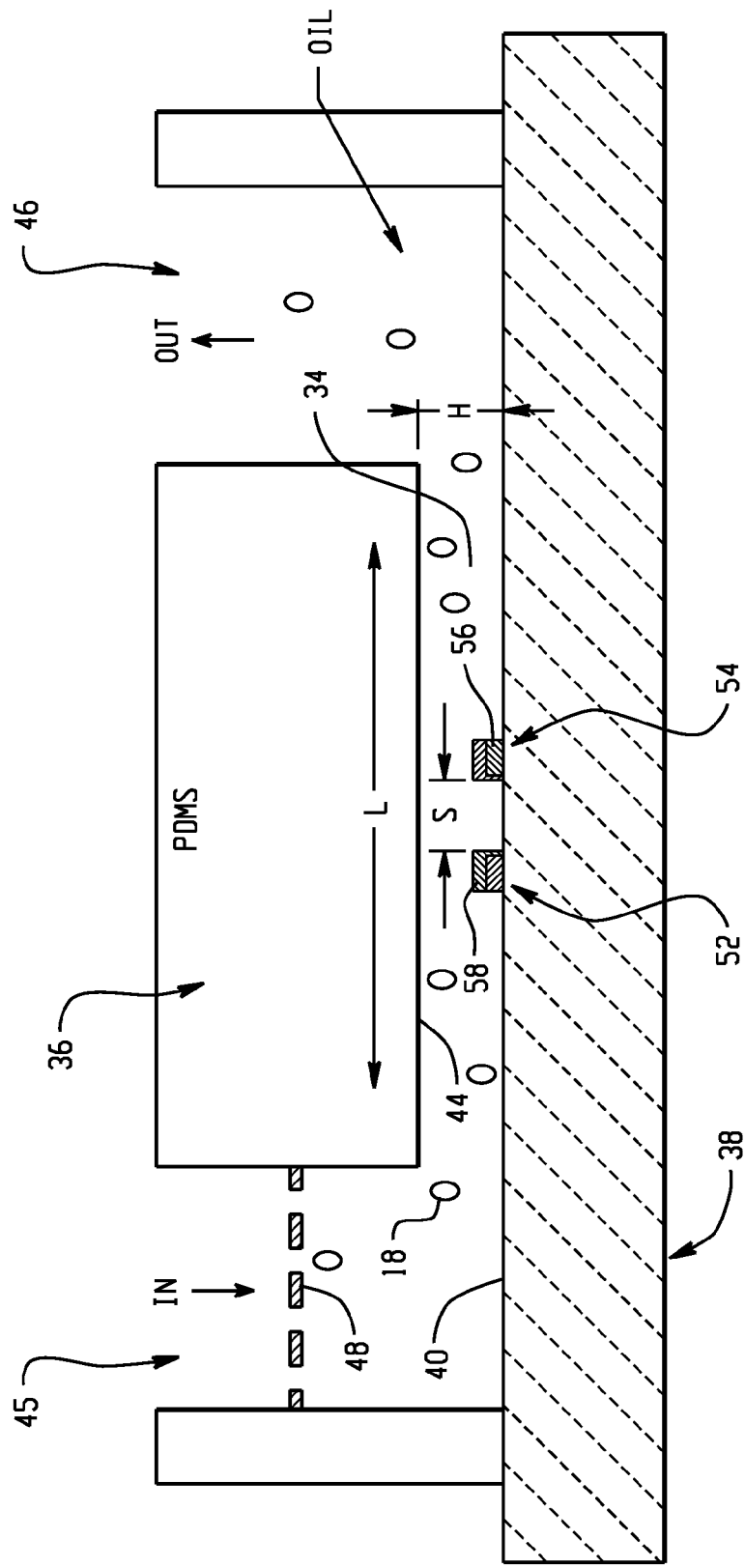
FIG. 3 is a cross sectional view of the microfluidic device of FIG. 1.

The illustrated microfluidic device 12 includes an inlet reservoir 30, in communication with inlet tube 20, an outlet reservoir 32, in communication with outlet tube 22, and a single fluidic microchannel 34. However, it is also contemplated that two or more microchannels may interconnect the two reservoirs 30, 32. The microchannel 34 has a height H, a width W and a length L, as illustrated in FIGS. 2 and 3. The microchannel represents a constriction between the two reservoirs 30, 32, in that the width W is less than the corresponding width w of each of the reservoirs. The height H and width W are selected to be sufficient to allow typical wear particles that are to be detected to pass therethrough. For example, H and W may each be at least 20 µm and can be up to about 200 µm. In one embodiment, the width W of the microchannel is greater than its height H. For example, $W \geq 2H$. This allows the particle to be off-centered from an axis x-x of the channel. For example, the dimensions of the microchannel may be about 40 µm (H)×100 µm (W)×300 µm (L) for detection of particles which are less than 40 μm. For detection of larger particles, the minimum dimension may be correspondingly larger.

As illustrated in FIG. 3, the exemplary microchannel 34 is defined in a polymeric body 36 that is supported by a substrate 38. A floor 40 of the microchannel is defined by the substrate 38. Opposed sides 42, 43 (FIG. 2) and a top wall 44 of the channel are defined by the body 36. The body 36 may also define an inlet channel 45 and an outlet channel, which extend generally perpendicular to the microchannel 34 (i.e., in the H direction). The inlet and outlet channels 45, 46 provide fluid communication between the inlet and outlet tubes 20, 22 and the respective reservoirs 30, 32.

The substrate 38 may be formed from glass or other electrically-insulative material. The body 36 may be formed by any suitable material which can be shaped, e.g., using lithographic or other techniques.

To ensure that the microchannel 34 does not become blocked with particles 18 which exceed its minimum dimension, a filter 48 may be positioned in the input path 14, e.g., in tube 20 (FIG. 1) or in inlet 45 (FIG. 3). The filter 48 may have a mesh size which is less than a minimum dimension H of the microchannel. For example, when H is 40 μm, the filter 48 filters out particles which exceed about 40 μm in size. e.g., filters out particles which exceed about 20 μm in size. The fluid path 14 may include a pump 50. Alternatively, the lubricated device 10 serves as a pump.

A pair of electrodes 52, 54 is disposed in the microchannel 34 for detecting microparticles. In the illustrated embodiment, the electrodes are coplanar, although in other embodiments, the electrodes may be vertically stacked, e.g., one on the top of the channel and one on the bottom. The illustrated electrodes are separated by a distance S of at least about 10 μm and up to about 100 μm, e.g., in the length direction L. The exemplary distance S can be about 20 μm when particles of less than about 20μ are to be detected. For larger particles, the spacing can be correspondingly larger to avoid a single particle from shorting out by contacting both electrodes. The exemplary electrodes 52, 54 extend in parallel, across the full width W of the microchannel 34, and may be about 5-10 μm in width (in the L direction). In one embodiment, the electrodes 52, 54 each have two planar layers 56, 58, which may be formed from conductive materials, such as Au and Ti, respectively. The lower layer 56 bonds the upper layer 58 to the substrate 38.

The electrodes are connected to a detection system 59 which detects wear particles as a function of capacitance changes between the electrodes. Specifically, as shown in FIG. 1, the electrodes 52, 54 have enlarged junctions 60, 62 at respective distal ends, which are connected by electrical leads 64, 66 to a detector 68, such as a MS3110 capacitance measurement chip. The detector 68 monitors capacitance between the two electrodes, or more particularly, changes in capacitance (ΔC) which may be measured in femtofarads fF ($10^{-15}$ farads) or picofarads pF ($10^{-12}$ farads). An analyzer 70, which is communicatively linked to the detector 68, periodically samples the voltage response of the detector (which is a function of the capacitance change) and determines a size of each particle and/or number of particles passing through the microchannel in a selected time interval, based on the capacitance changes/voltage responses which exceed background noise (pulses). The magnitude of the capacitance pulse increases with increased particle size; thus the pulse height is indicative of the particle size. The exemplary analyzer 70 is communicatively linked to a signaling device 72, such as an audible signaling device (e.g., a loudspeaker) or a visual signaling device (e.g., a visual display). If the size of the particles and/or number of the particles reaches a predetermined threshold which is indicative of unacceptable wear or need for a device service, the analyzer 70 communicates the condition to the signaler 72 which emits an audible or visual signal. An operator passing by notices the signal and can perform suitable operations on the device 10 to correct the condition. Alternatively or additionally, the analyzer outputs a wear index or other measurement to the signal which provides an indication as to the number and/or size of wear particles in the device lubricant.

During operation of the microfluidic device 12, with the channel horizontally orientated as shown, as a metal particle 18 passes through the microchannel, it causes a change in the capacitance (ΔC) formed by the two coplanar electrodes 52, 54. The particles 18 are detected one at a time as they pass through the microchannel 34 as pulses in the AC. The magnitude of the pulses is generally in the range of 2 to 10 femtofarads. The variation of the capacitance change is observed due to the off-axis passage of the particles through the microchannel 34. The signaling device 72 provides a visual or audible signal in response to a detection of wear particles which exceed at least one of a threshold size (e.g., exceed an average or maximum size) and a threshold number (e.g., in a selected time interval, such as one minute).

The exemplary detector 68 may sense the change in the differential capacitance and provide an output voltage proportional to that change. The differential measurement allows a compensation for the parasitic capacitances. The change in output voltage in terms of the capacitance change of microchannel may be given by the expression $$\Delta V = K \cdot \frac{\Delta C}{C_F}$$

where K is a constant proportional to the gain setting and the reference voltage, ΔC is the change in sensing capacitance (microchannel capacitance) and $C_F$ is the feedback capacitance of the detector.

In another embodiment (not shown) the microfluidic device includes a plurality of microchannels 34. Each of the microchannels may have different dimensions. A multi-channel device is disclosed, for example, in Zhe J., Jagtiani, A. V, Dutta P., Hu J. and Carletta J, 2007, A micromachined high throughput Coulter counter for bioparticle detection and counting, *Journal of Micromechanics and Microengineering*, 17, pp. 304-313. This allows detection of debris of different sizes. A particle separator may be positioned between the inlet 45 and the microchannels. The separator steers individual particles to the detection microchannel of appropriate size. The throughput of the device 12 can also be significantly improved by using multiple microfluidic detection channels 34 of the same and/or different sizes operating in parallel.

In the illustrated embodiment, the microfluidic device is directly connected with the lubricated device 10 by a fluid pathway 14. In other embodiments, a sample of oil may be taken from the lubricated device 10 and injected or otherwise introduced to the microfluidic device.

Device Fabrication

The use of co-planar electrodes 52, 54 allows a simplification of the micromachining of the device. The microchannels and reservoirs may be fabricated in a layer of polydimethyl-siloxane (PDMS) or other polymeric insulative material, using soft lithography. The PDMS mold is then bonded to a glass substrate on which Au/Ti electrodes have been formed.

The pattern for the microchannel and the reservoirs may be fabricated using a negative photoresist, e.g., an octafunctional epoxidized novolac resin, such as SU-8 or variant thereof. An exemplary formation method is illustrated in FIG. 4. At S100, a layer 80 of the negative photoresist may be deposited on a substrate 82, using a suitable deposition technique, such as spin coating, to a thickness of at least the desired height H of the microchannel. For example, the negative photoresist may be spin coated onto a microscope glass slide 82 at 2000 rpm to achieve a thickness of 40 µm. The photoresist may be patterned with light of an appropriate wavelength, such as UV light to define the reservoirs and channel (S102). A layer 84 of PDMS is then poured over the mold and cured to transfer the desired pattern onto the PDMS (S104).

To fabricate the electrodes 52, 54, a glass substrate 38 may be coated with a layer of 90 of titanium and a layer 88 of gold (S108). The layers may be patterned with a positive photoresist 92, such as one employing an o-quinone diazide radiation sensitizer, such as AZ®-P4620 available from Clariant Corp., Somerville, N.J. The electrodes are formed by exposure of the photoresist to light of a suitable wavelength, such as UV light, and a developer, followed by etching of the Au and Ti layers (S110). The device 12 may be completed by bonding the PDMS layer 36 to the electrode slide, e.g., by heat activation of the surfaces, e.g., in an air plasma.

2. Impedance Detection Method

In another embodiment, rather than monitoring capacitance, the change in inductance of a coil embedded in the microchannel can be measured. A metal particle passing through the microchannel causes a change in the inductance of the coil owing to 1) the difference in magnetic permeability between the lubrication oil and the metal particle, and 2) eddy current generated inside the metal particle.

The particle couples with the magnetic field to varying degrees as it traverses the sensing region, resulting in changes in inductance output, in terms of magnitude and phase. External detection electronics determine the amplitude and phase of the output signature, which can be used to identify the size and nature of the particle. Because of the different response between ferrous and non-ferrous particles, the device can differentiate between ferrous and non-ferrous particles.

Figure 5:
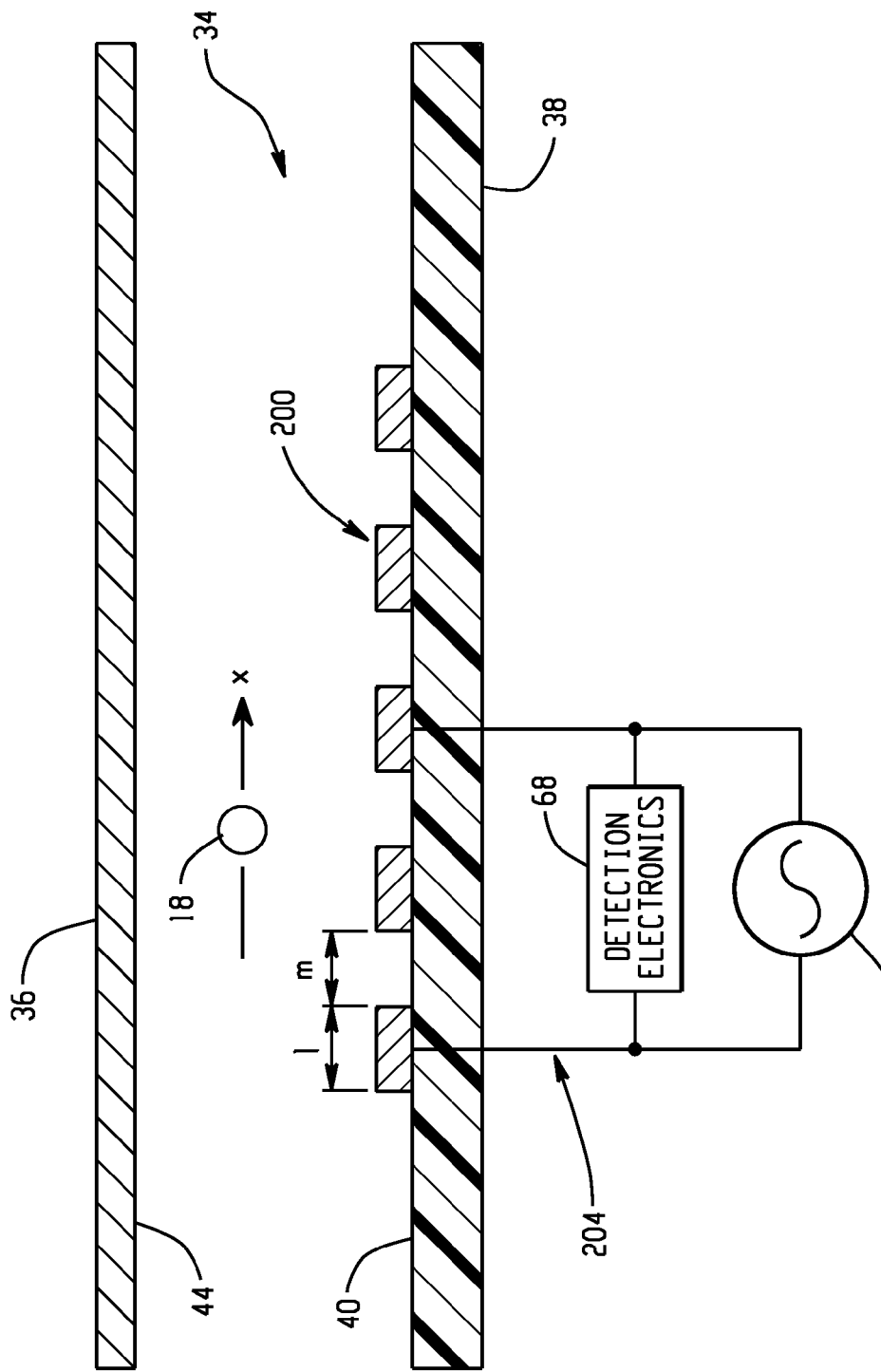
FIG. 5 is a schematic side view of a microchannel of a microfluidic device in accordance with another aspect of the exemplary embodiment with a coiled electrode which may be used for inductance measurements in an apparatus analogous to that of FIG. 1.
Figure 6:
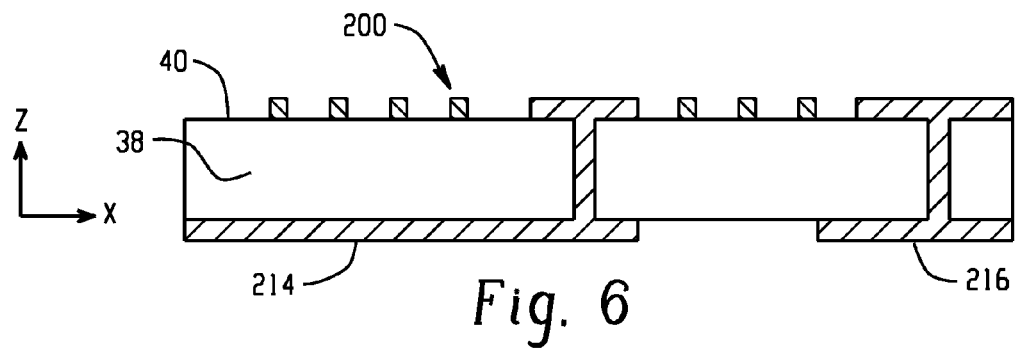
FIGS. 6-8 show side, top, and bottom views, respectively of a substrate with a solenoid imprinted thereon which may be employed in the device of FIGS. 1 and 5.
Figure 7:
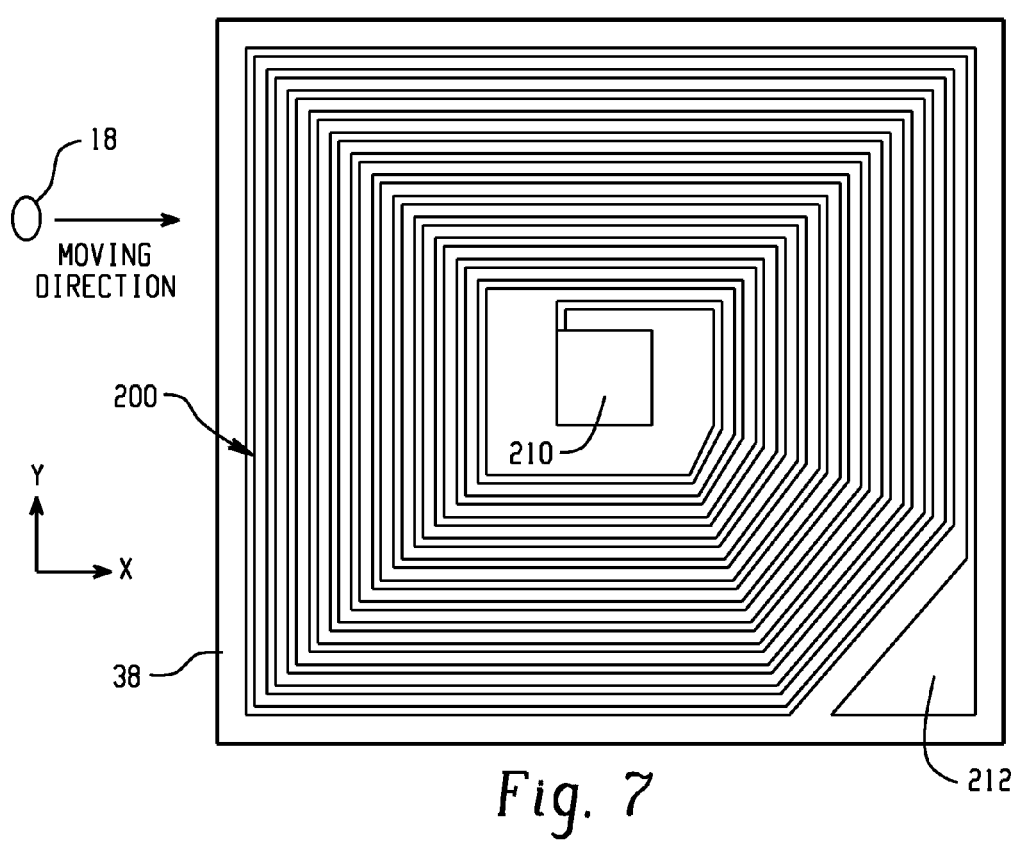
Figure 8:
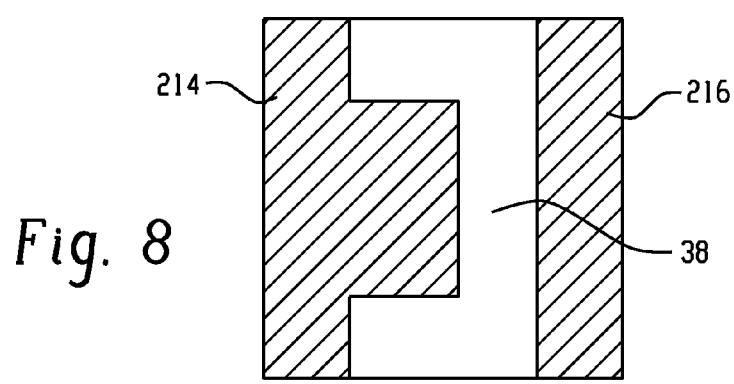

FIG. 5 illustrates an inductive Coulter counting microfluidic device which can be configured similarly to the device of FIGS. 1-3, except as noted. In this embodiment, the pair of electrodes is replaced by a single electrode in the form of an excitation coil 200. For a micro-scale device, a planar solenoid coil 200 may be carried on a substrate 38, which defines a bottom wall of the channel 34. An external oscillator, such as an AC source 202, supplies an alternating current to the solenoid 200 via a circuit 204. FIGS. 6-8 provide side, top, bottom, and bottom views of the substrate 38 and coil 200.

The source 200 may be one which is able to provide a frequency of oscillation in the range of about 2 Hz-20 MHz, e.g., 100-600 KHz. When a metal particle 18 passes through the microchannel 34, it causes a detectable change in impedance of the solenoid 200 which is detected by device electronics 68 connected across the solenoid 200. In this embodiment, the lubricant oil flowing through the microchannel 34 carries the particles 18 in the horizontal direction of arrow x, i.e., parallel to a plane of the coil 200.

The coil 200 may be formed from copper or other conductive metal. The substrate 38 may be formed from a dielectric material such as a ferrite (e.g., a nickel-zinc oxide). A ferrite coating or substrate on the coil, which may also occupy the spacing between turns of the coil, can enhance the magnetic field, improve the sensitivity, and help reduce environmental noise by providing magnetic shielding.

Ferrites are usually non-conductive ferrimagnetic ceramic compounds derived from iron oxides, such as hematite ($Fe_2O_3$) and/or magnetite ($Fe_3O_4$), as well as oxides of other metals. The proportion of iron oxide in the ferrite may vary, but is generally in the range of 30-60 wt %. Two exemplary ferrite materials are: a) Mn—Zn ferrite: which is about 50 wt. % iron oxide, the remainder consisting primarily of mixed oxides of manganese and zinc, and b) Ni—Zn ferrite: which is about 50 wt. % iron oxide, the remainder consisting primarily of oxides of nickel and zinc.

The coil 200 defines a continuous strip with a plurality of concentric turns. To optimize detection of very small particles, it is desirable for the coil to have as many turns as possible in as small an area as possible. The coil may include at least 5 turns and in one embodiment, at least 10 turns. While in FIG. 7, the turns are illustrated as being substantially rectangular, in other embodiments, the turns may be circular. As shown in FIG. 5, the turns of the coil 200 may have a line width l of about 2 µm or greater (i.e., sufficient width to carry an electric current for producing a magnetic field) e.g., up to about 50 µm. A spacing in between turns of the coil may be about 2-100 µm, e.g., 5-10 µm. Respective ends 210, 212 of coil 200 are connected through the substrate with contacts 214, 216 (FIGS. 6 and 8) for interconnection with the AC source 202. When a metal particle 18 moves close to the top surface of the planar coil 200, an inductance change occurs because of the changes in magnetic permeability and eddy current. A ferrous particle 18 causes a positive change in inductance while an aluminum particle 18 causes a negative change in inductance.

The planar configuration of the coil allows for ease of fabrication due to the difficulty of three-dimensional microscale fabrication. As with the capacitative sensing device, a microfluidic device may be formed with multiple channels for high throughput online wear debris monitoring. For a larger scale device, the coil 200 may be formed in three dimensions by wrapping a wire around the channel wall (see FIG. 9).

Figure 9A:
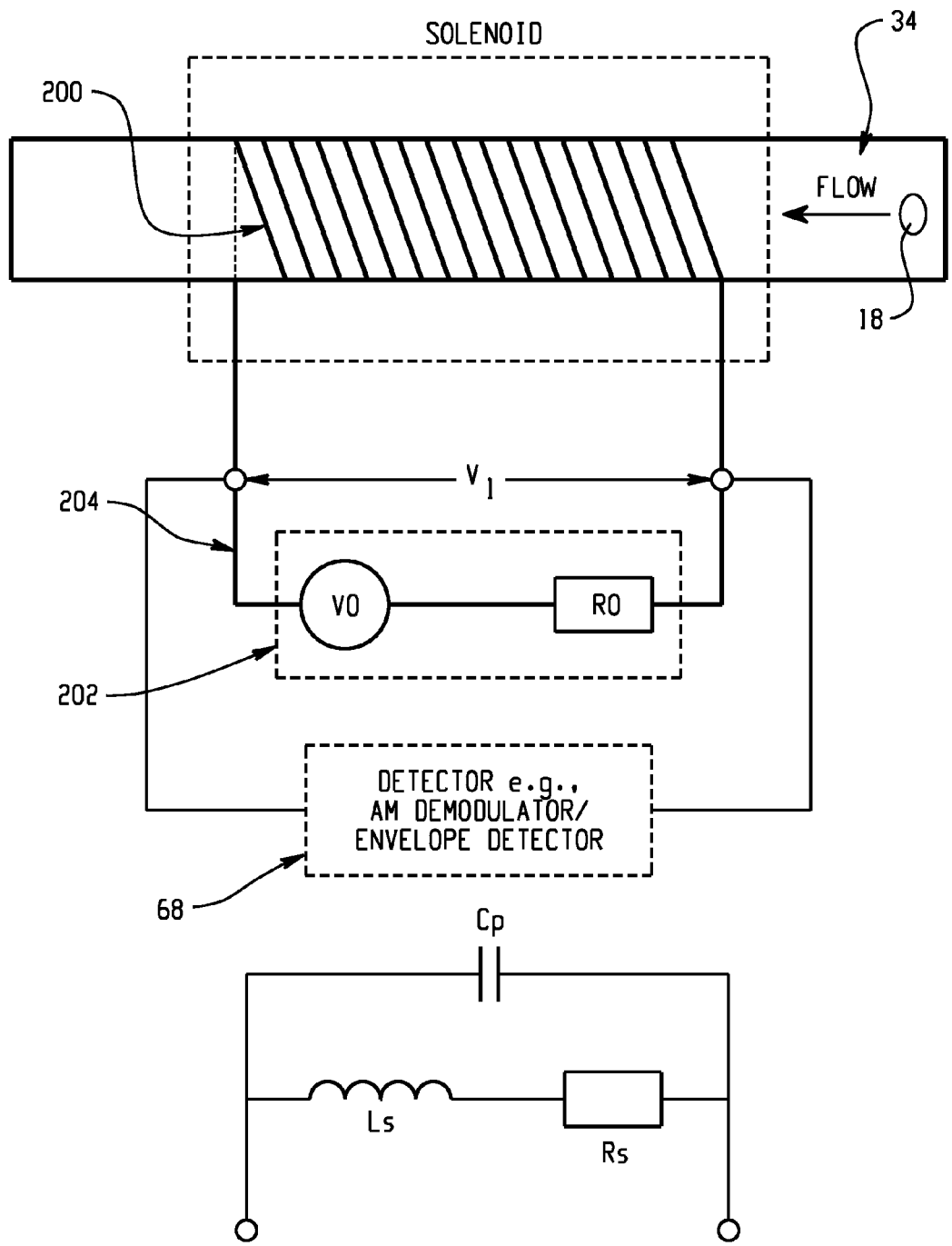
FIGS. 9A and 9B illustrate exemplary detection circuits for the detection of inductance in the device of FIG. 5, in FIG. 9A, amplitude/phase angle changes are measured, in FIG. 9B changes in oscillating frequency are measured.
Figure 9B:
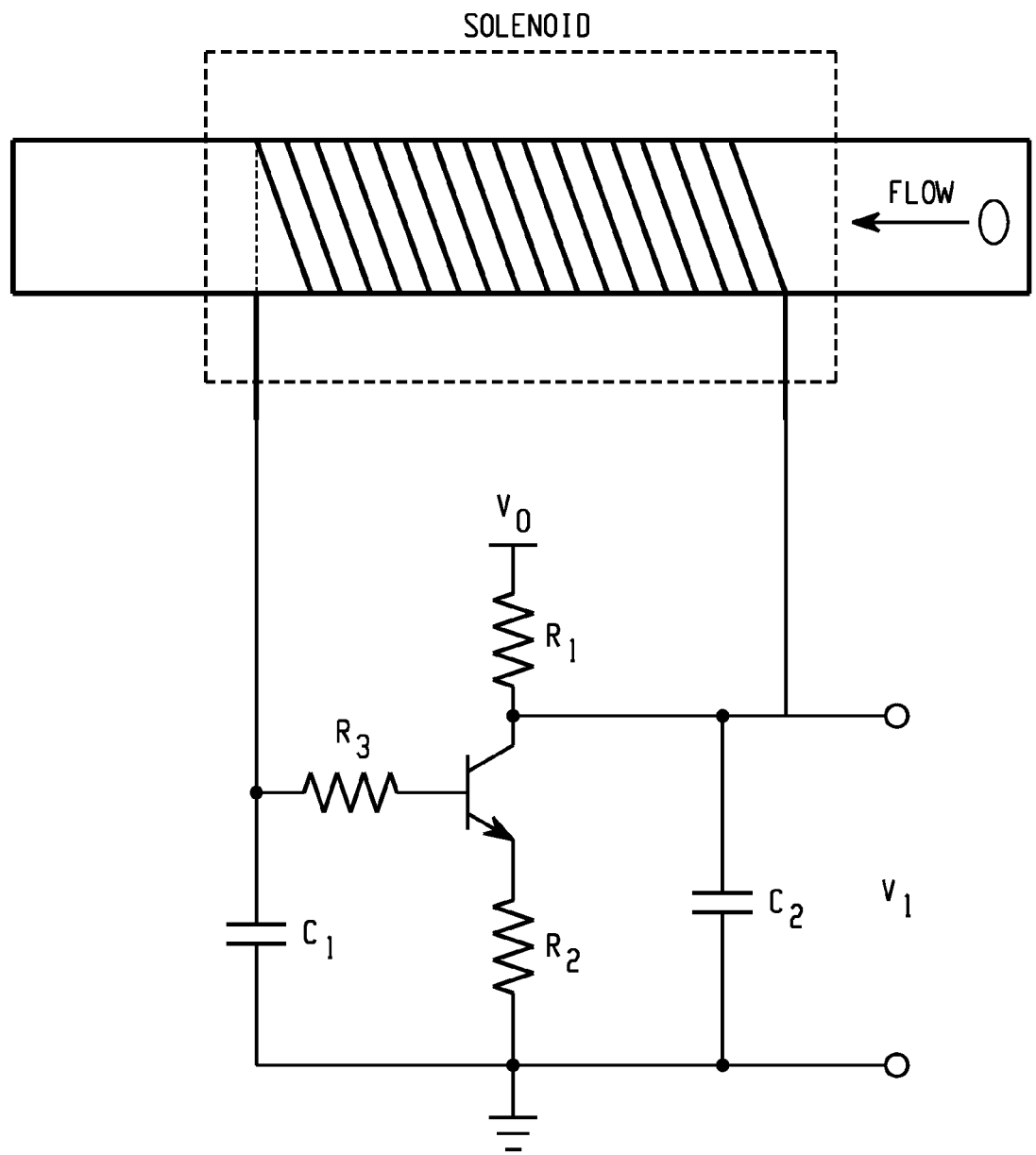

FIG. 9A illustrates the operation of the system. R0 is the internal resistance of the AC source 202. In the equivalent circuit of the solenoid, $L_s$ is the inductance of solenoid 200, $R_s$ is the DC resistance of the solenoid, and $C_p$ is the parasitic capacitance between the turns of the solenoid. In practice, the resistance $R_s$ and capacitance $C_p$ of the solenoid coil remain relatively constant. Thus, the measured voltage $V_1$ across the solenoid coil 200 is primarily dependent on changes in inductance $L_s$ of the coil. In this embodiment, an amplitude/phase angle measurement is made. Detector 68 may thus comprise an AM demodulator or envelope detector to measure the magnitude/phase angle of the coil output $V_1$. From the measurements, the detector may be able to detect an inductance change of less than 0.1 nanoHenry.

In another embodiment (FIG. 9B), the planar coil 200 is included in an oscillator circuit for which the frequency of oscillation depends on the value of the coil inductance. Three resistors $R_1$, $R_2$, $R_3$ are used as biasing components. $V_0$ represents a DC power supply/source. An oscillator consisting of the coil and capacitors $C_1$ and $C_2$ with fixed capacitance C can generate a frequency. The change of L due to passage of a particle will cause a change/shift of oscillating frequency. In such a circuit, the passage of a debris particle 18 through the channel modulates the frequency of the output voltage $V_1$. In the circuit shown, the frequency of oscillation can be expressed as $\sqrt{2/LC}$, where L is the variable inductance, and C is the capacitance of each of the two fixed capacitors $C_1$ and $C_2$ in the circuit. The circuit is only an illustration of the principal components of an example oscillator circuit, and does not show ancillary components which are present for biasing and power supply.

Other instrumentation schemes are contemplated and may include, for example, single-ended or differential amplifier circuits excited at a fixed frequency, for which the passage of a particle would modulate the amplitude of the output voltage.

Figure 12:
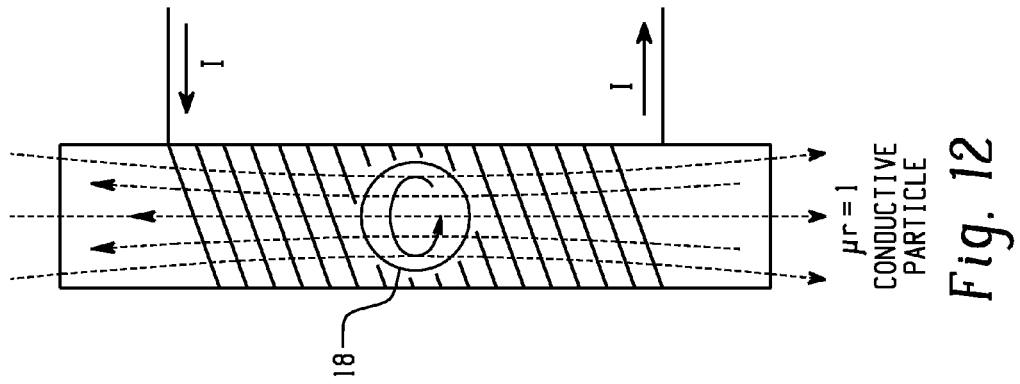
FIGS. 10-12 illustrate the magnetic field induced in the solenoid of an inductive Coulter Counting device due to a current passing through solenoid (FIG. 10); magnetic flux enhancement due to presence of a ferrous particle (FIG. 11); and magnetic flux attenuation due to eddy currents generated in a conductive particle (FIG. 12)
Figure 11:
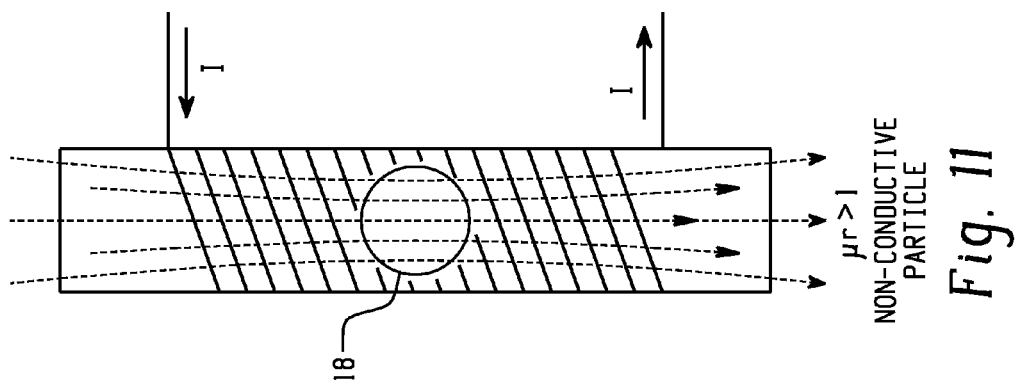
Figure 10:
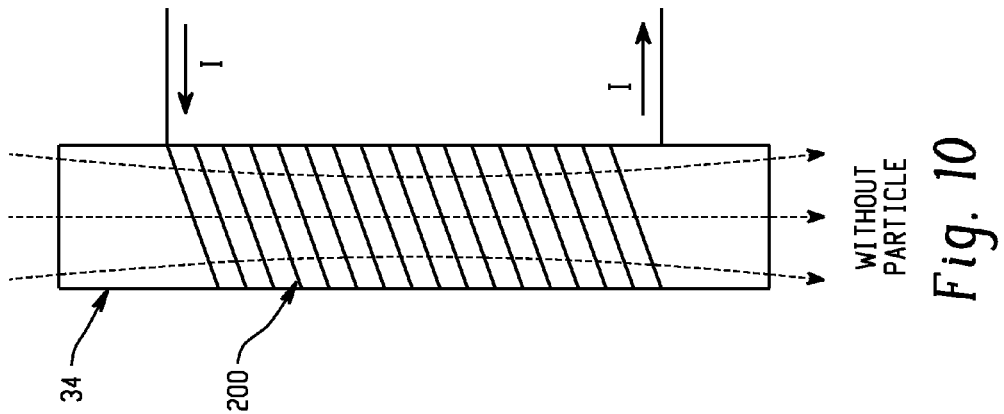

As illustrated in FIGS. 10-12, an AC voltage is applied across the solenoid (here shown as a three dimensional coil but equally applicable to a planar coil), and induces a magnetic field in the solenoid. The ideal source voltage is divided between the internal resistance of the voltage source and the impedance of the solenoid, so that the voltage across the solenoid ($V_1$) depends on the solenoid's impedance. Any change in impedance of the solenoid induces a change in $V_1$. If a ferrous but nonconductive particle 18 (with relative magnetic permeability $\mu_r$ significantly higher than that of lubrication oil) is introduced into the microchannel, the magnetic flux is enhanced (FIG. 11), causing an increase in inductance $L_s$ and an increase in $V_1$. On the other hand, if a conductive but nonferrous particle is introduced into the microchannel, an eddy current is generated inside the metal particle in a way that opposes the original magnetic field (FIG. 12); as a result, the total magnetic flux is decreased, leading to a decrease in the inductance $L_s$ and in the output voltage $V_1$. The higher the frequency of the AC excitation, the larger the eddy current and therefore the larger the drop in the inductance $L_s$ and in the output voltage $_{V1}$.

The two factors, magnetic permeability and eddy current, contribute to $L_s$ and the output voltage $V_1$ in competing ways if a particle is both ferrous and conductive. At low frequencies, the eddy current is small, and the impedance increase caused by the change in magnetic permeability is dominant; thus, passage of a particle generates a positive voltage pulse. At high frequencies, the eddy current effect is dominant, and passage of a particle leads to an overall reduction in $L_s$ and a negative voltage pulse. Therefore ferrous and nonferrous debris can be differentiated by looking at pulse polarity at an appropriate frequency.

FIG. 13 shows another embodiment of an inductive Coulter counting microfluidic device which can be configured similarly to the device of FIG. 5, except as noted. In this embodiment, the detection circuit 68 measures a change in voltage/inductance in a detection coil 220. The detection coil 220 is spaced from the excitation coil 200 by the channel, and may be embedded in an upper wall 44 of the channel directly above the coil 200. The configuration of the detection coil 220 may be the same as that of the excitation coil 200 shown in FIGS. 6-8, except that it is inverted. Both coils 200, 220 may be in contact with the liquid passing through the channel 34.

Figure 14:
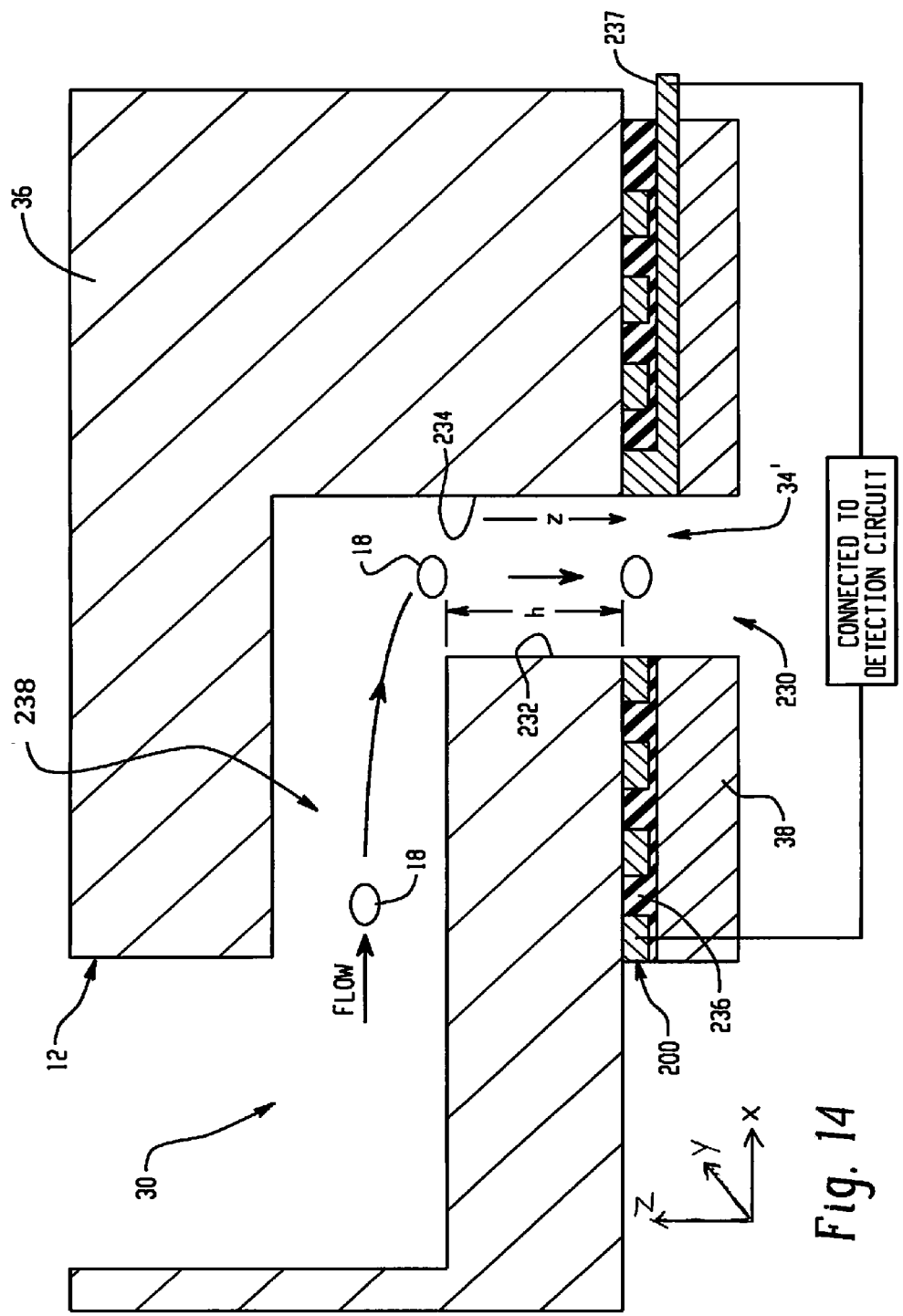
FIG. 14 is a schematic side view of a microfluidic device with a vertical microchannel of in accordance with another aspect of the exemplary embodiment with a coiled electrode and separate detection circuit which may be used for inductance measurements in an apparatus analogous to that of FIG. 1.

FIG. 14 shows another embodiment of an inductive Coulter counting microfluidic device which can be configured similarly to the device of FIG. 5, except as noted. In this embodiment, microchannel 34' is arranged perpendicular to the x-y plane of the coil 200 such that the particles 18 are carried in a vertical direction z towards (or away from) the coil 200. In this embodiment, a hole 230 in the substrate 38 allows the fluid to pass through the center of the coil 200. Although not shown, an excitation source and detection circuit supply and measure a change in voltage/inductance in the coil 200, respectively. The vertically extending channel 34' has side walls 232, 234 spaced to minimize the chance that more than one particle 18 can pass side by side through the channel. It has been found that the inductance is a function of the distance of the particle from the detecting coil 200. In this embodiment, it is known that every particle will at some point be a distance h above the x-y plane of the coil and a later time will be level with the x-y plane where the change in inductance will reach a peak (maximum or minimum). Thus, the maximum detected inductance change can be used to calibrate the detection system with particles of known size and, in use, to detect the size of particles. The vertical channel also has an advantage in that fluctuations in inductance as the particle moves in the x direction are minimized.

In this embodiment, the microchannel 34' (or a plurality of microchannels), can be formed in a body 36 formed from a polymeric material or silicon. The vertically extending channel 34' can be entered from a horizontal channel 238 in the body, at a distance h above the coil 200, in which particles 18 flow generally parallel with the substrate 38. The distance h can be selected such that particles 18 in channel 238 have little or no influence on inductance measurements.

The magnitude and the shape of the detected pulses as the particle passes through the coil are indicative of particle's size and shape, respectively. By measuring inductive pulses, changes in flow rate and temperature of the lubrication oil, as well as environmental noise due to parasitic inductance and capacitance, affect only the baseline inductance, and thus can be factored out.

The device 10 may be fabricated as follows. One or more microchannels 34, 34' can be formed in a support body 36 using a dry etching or wet etching method. The support body 36 may be a silicon wafer or formed from ceramic or other solid materials that are compatible with etching/micromachining techniques. A metal (e.g., titanium and/or gold) thin film is deposited on a surface 235 of the support body 36. Planar microcoils 200 are formed on the other surface of the silicon wafer (one coil for each channel 34'). The fabrication of the planar coil may include three sub-steps: a) fabrication of coil turns, e.g., with photolithography, b) formation of an insulation layer 236 and a top lead strip 237 to trace the inner contact of the coil out, and c) deposition and patterning of a high-resistivity Ni—Zn ferrite layer 38 on top of each coil 200 for enhancing the base inductance. Silicon oxide, silicon nitride, aluminum oxide, or the like can be used for forming the insulation layer 236.

Photolithography may be used to fabricate the coil 200 on the metal layer. The ferrite 38 layer may be deposited onto the support body 36, overlying the coil 200. The deposition of the ferrite may be performed by spraying a reaction solution of $FeCl_2+NiCl_2+ZnCl_2$ and an oxidizing solution of $NaNO_2+CH_3COONH_4+NH_4OH$. The Ni—Zn ferrite film can be patterned by Ar sputtering etching or chlorine-based reactive sputtering etching. $Al_2O_3$ can be used as the masking material.

Figure 15:
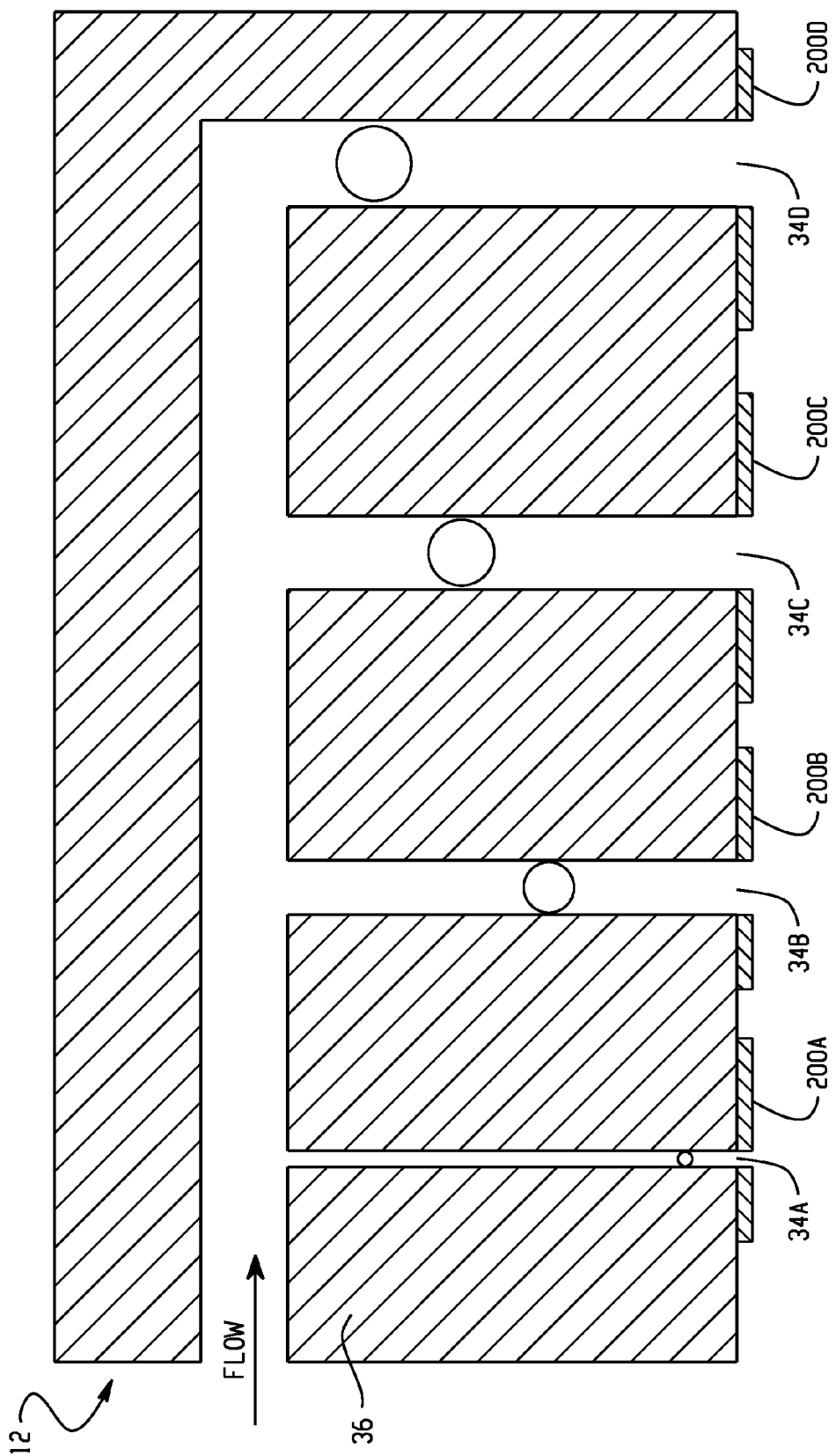
FIG. 15 illustrates a multichannel microfluidic device.

As illustrated in FIG. 15, in a multichannel device, which may be formed analogously to the device of FIG. 14, the metal particles 18 are separated by size into streams, and each stream is sent through its own appropriately sized detection channel 34A, 34B, 34C, 34D, so that the particles in a stream pass one by one through the center of a respective planar coil 200A, 200B, 200C, 200D. Each coil may be excited at a respective frequency appropriate for detection of particles in the size range expected.

To select appropriate excitation frequencies to differentiate particular magnetic and nonmagnetic metals, a mathematical model can be developed to predict the inductance change due to the passage of a metal particle, assuming a generally spherical shape. The mathematical model can consider the effects of the particle's magnetic permeability, conductivity, and size, at different excitation frequencies.

Figure 16:
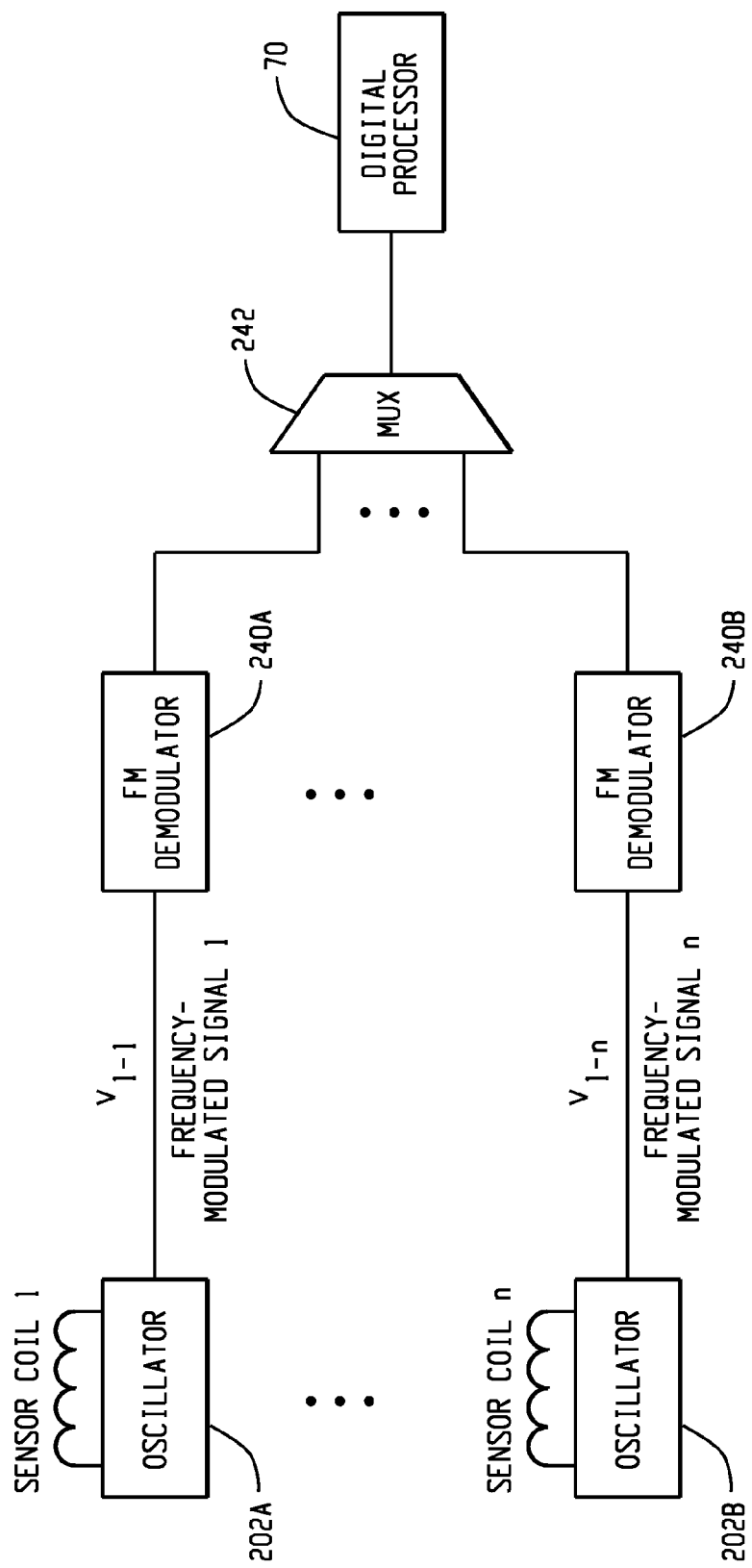
FIG. 16 illustrates a detection electronics for the multichannel microfluidic device of FIG. 16.

While FIG. 15 only shows four microchannels, there may be many more microchannels, e.g., arranged in an array. If there are a large number of channels, e.g., about 100, it becomes complex to monitor the measurement pulses of each channel individually. Multiplexing techniques can thus be used for multichannel measurement. As shown in FIG. 16, demodulation of the FM signals by demodulators 240A, 240B produces the voltage pulses representing the passage of wear debris particles through the sensors. To achieve sufficient sensitivity, the demodulator circuits may include phase-locked loops. The demodulated pulses representing the particles passing through each separate sensor may be combined on a single digital or analog channel by a multiplexer 242. The multiplexer may include digital hardware or software to store the information about the pulses, to convert the information to a digital format, and to gate the digital information onto a digital communication channel. An alternative multiplexer implementation may make use of frequency division for combining the sensor information on a single analog channel. The set of outputs from the inductive detectors is combined into a single signal. The combined signal is transmitted to a digital processor 70 which then separates the signals and interprets their content.

Without intending to limit the scope of the exemplary embodiment, the following examples demonstrate the applicability of the apparatus and method to detection of wear particles of ferrous and non-ferrous materials.

EXAMPLES

Example 1

Meso-Sized Capacitative Sensing Device

Figure 17:
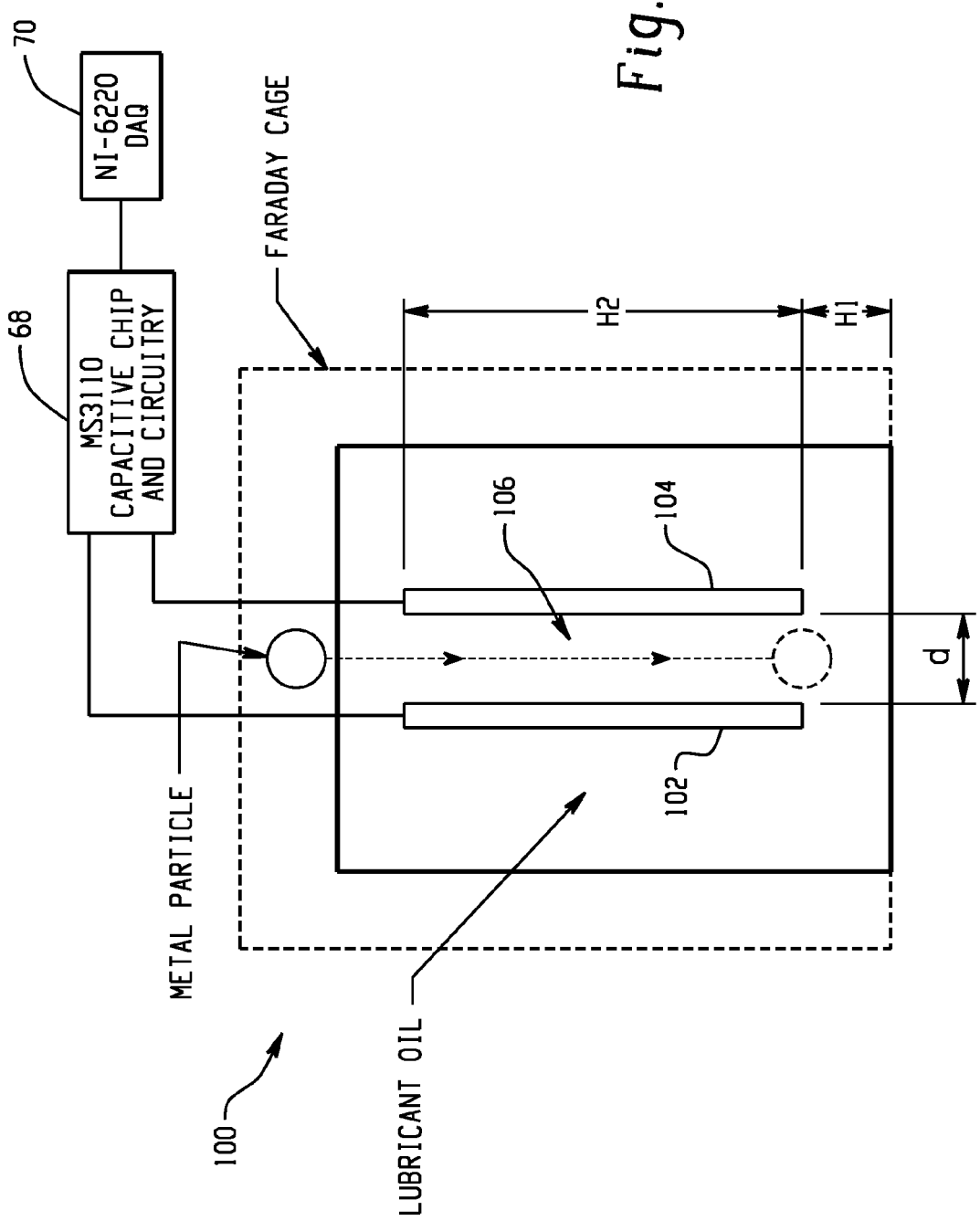
FIG. 17 illustrates an exemplary arrangement for testing the ability to detect particles in a lubricant using capacitance measurements.

A meso-sized device 100 for testing the applicability of the apparatus to lubricant oils was constructed, as illustrated in FIG. 17. The device 100 consists of two parallel aluminum plates 102, 104 (cross section 2.5 cm (H)×4 cm (W)) forming a channel 106 therebetween. The plates were immersed in SAE-5W30 motor oil (with a relative permittivity $\in_r$ ranging from about 2.1 to 2.4). Three spherical steel particles (diameters D=3.5 mm, 4.5 mm and 6.0 mm, obtained from McMaster-Carr, USA) were dropped from the top of the channel and allowed to travel to the bottom. A capacitive readout MS3110 IC chip 68 (obtained from Irvine Sensors, USA) and a NI-6220 data acquisition system (DAQ) 70 (obtained from National Instruments, USA) were used for the dynamic capacitance measurement as each particle passed through the channel 106.

The MS3110 IC chip senses the change in the differential capacitance and provides an output voltage proportional to that change. The differential measurement eliminates problems with the direct measurement of capacitance in the presence of large parasitic capacitances. The change in capacitance in terms of the measured voltage is given as:

$$\Delta V = K \cdot \frac{\Delta C}{C_F}$$

where K is a constant proportional to the gain setting and the reference voltage of the MS3110 chip, $\Delta C$ is the sensing capacitance change and $C_F$ is the feedback capacitance. For these experiments, K was 5.13 and feedback capacitance $C_F$ was 1.197 pF.

Figure 18A:
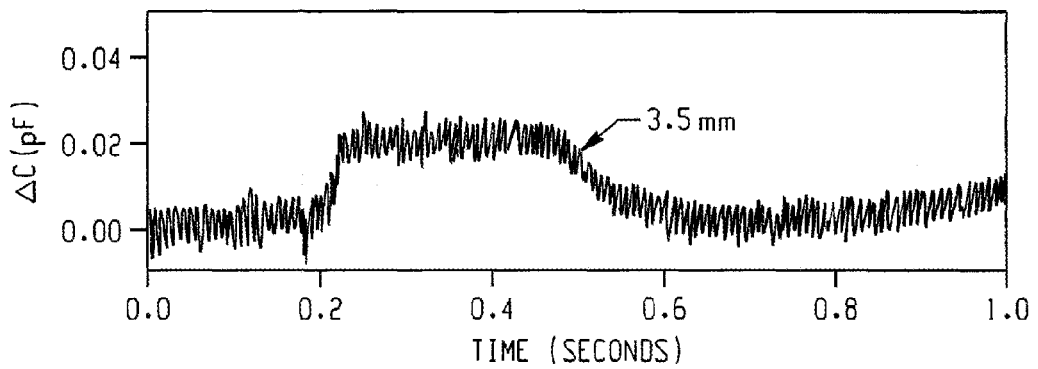
FIG. 18 is a plot of change in capacitance over time during the passage of a particle through the device of FIG. 17 for particles of different sizes.
Figure 18B:
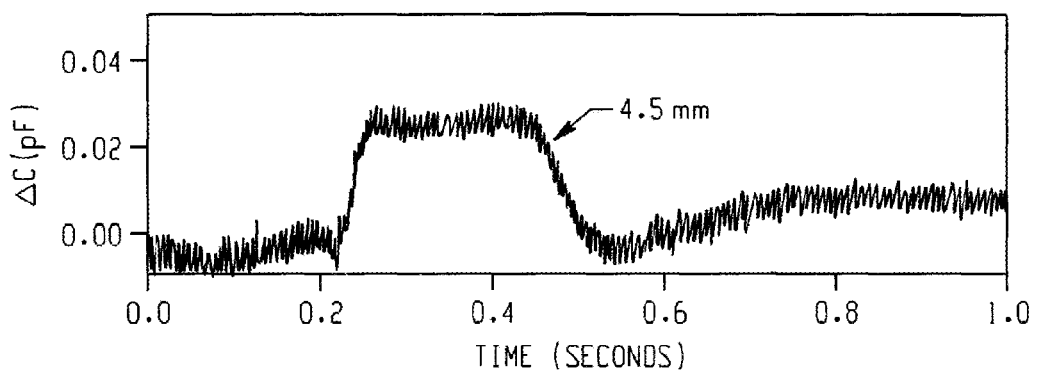
Figure 18C:
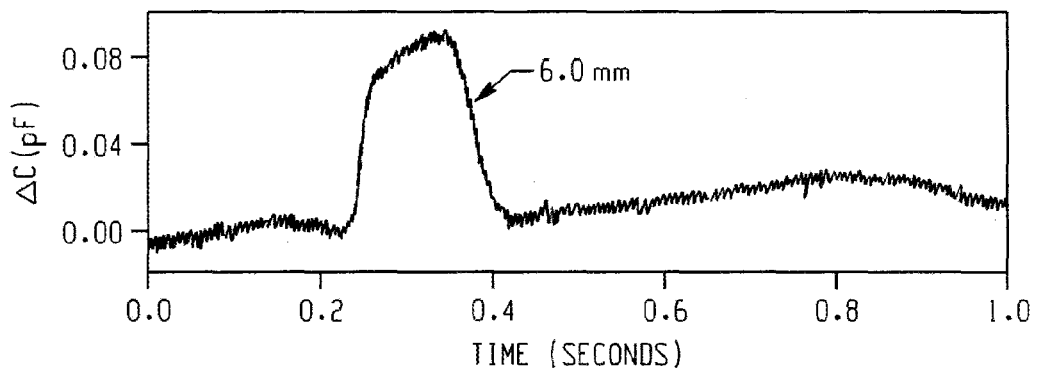

In a first experiment, the distance d between the two plates was set at 1 cm and there was no gap between the electrodes and the bottom of the oil container (H1=0). As shown in FIG. 18, the capacitance change increased as the particle size is increased. The pulse width decreases with increased particle size because a heavy particle travels through the vertically orientated fluid channel faster.

In a further experiment, the spacing (d) between the two parallel electrodes 102, 104 was reduced to 0.45 cm and both electrodes raised 1 cm above the bottom (H1-1 cm). This better mimics a Coulter counter, in which the particle passes completely through the channel. A 2.3 mm metal particle was dropped from the top of the channel. A capacitive pulse due to the passage of particle through the channel was observed. Both tests demonstrated the feasibility of using a capacitance-based Coulter counting principle for metal wear detection.

Similar testing was also carried out using aluminum and solder (an alloy of lead) particles. No noticeable difference in capacitance change was found among different metals particles with same size.

Figure 19:
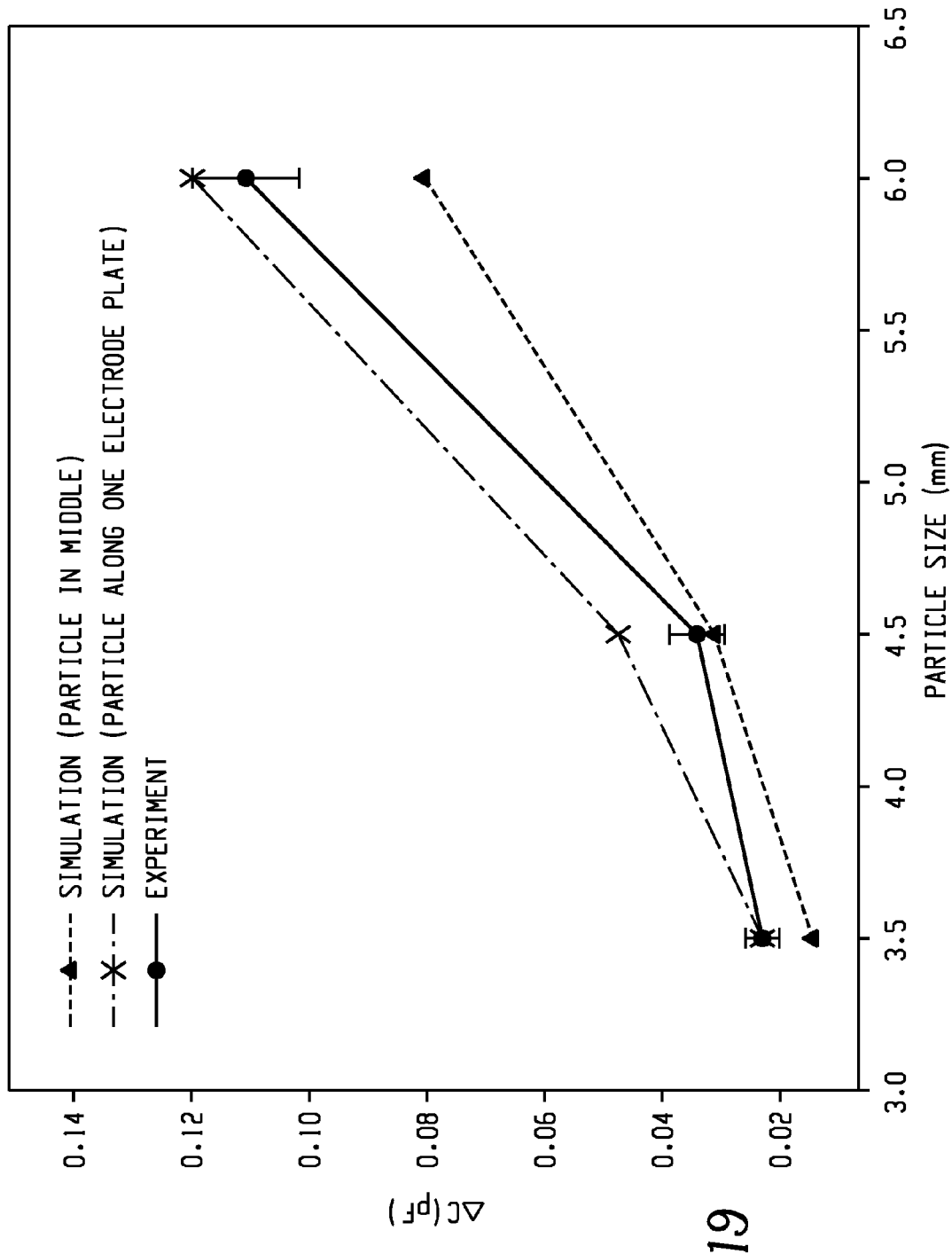
FIG. 19 is a plot illustrating the effect of particle size on change in capacitance over time compared with theoretical plots generated by FEM simulation.

The measured capacitance changes are in good agreement with the theoretical prediction using a model developed by Sarid (See, Sarid D., 1994, Scanning Force Microscopy, Oxford University Press, US, pp 129-152), as illustrated in FIG. 19. For this study, finite element (FEM) simulation also conducted for the microfluidic device to predict the capacitance change. Finite element simulation of the mesoscale device was performed to predict the capacitance change for each of the particle sizes. The simulation was conducted using COMSOL Multiphysics 3.4 under electrostatic mode in the AC/DC application module. A mesh-independent result was obtained by using 55000 elements. The simulation was validated by showing that simulation results for the self-capacitance of a conducting sphere (a similar problem with an analytical solution) match theoretical prediction well. The boundary conditions for the two electrodes are set as port and ground, forcing the boundary potentials to normalized values of one and zero, respectively. The metal particle is modeled as a sphere with a floating potential boundary condition. The relative permittivity of SAE5W-30 oil ranges from 2.1 to 2.4. For the simulation, a value of 2.3 was assumed.

The capacitance change depends on the position of the particle as it passes through the fluidic channel; a particle traveling along the centerline midway between the electrodes causes the least change, and a particle traveling close to (but not touching) one of the electrodes causes the most change. Thus, simulation of a centered particle is used to determine a lower bound on the capacitance change, and simulation of a particle at the electrode is used to determine an upper bound. FIG. 19 shows simulation results for the range of capacitance changes, with lower and upper bound curves as a function of particle size. The figure also shows the capacitance changes seen with the experimental device, with error bars to show the range of capacitance changes seen over the course of ten experiments. The simulation and experimental results agree fairly well. Because it is difficult to control an experimental particle's trajectory, it is expected only that the measured capacitance change fall between the lower and upper bound simulation points for a particle of that size. These results on a mesoscale device demonstrate the feasibility of using a capacitance-based Coulter counting principle for metal wear detection.

Example 2

Microscale Capacitive Sensing Device

Having established the viability of the capacitive sensing technique with relatively large particles as described in Example 1, a microfluidic device 12 for detecting microscale debris particles in the lubricant oils was constructed as illustrated in FIGS. 2 and 3. The device consisted of an inlet reservoir, an outlet reservoir, a single fluidic channel 34 with dimensions of 40 µm (H)×100 µm (W)×300 µm (L), and a pair of co-planar electrodes 52, 54 for detecting microparticles 18, separated by a distance S of 20 µm. The particles were detected one at a time as they passed through the microchannel 34. The electrodes 52, 54 were connected to a MS3110 capacitance measurement chip 68, and the voltage response from the MS3110 was monitored using a NI-6220 DAQ 70.

2.1: Device Fabrication

The fabrication of the device 12 involved microchannel fabrication and electrode fabrication. The microchannels and reservoirs were fabricated on polydimethylsiloxane (PDMS) using soft lithography, as illustrated in FIG. 4. The pattern for the microchannel and the reservoirs was fabricated using a negative photoresist, SU8-2025 (MicroChem. Inc., USA). The photoresist was spin coated onto a microscope glass slide at 2000 rpm to achieve a thickness of 40 µm. The glass slide was soft baked at 65° C. for three minutes and at 95° C. for six minutes. The photoresist was exposed under UV light at an exposure dose of 224 mJ cm$^{-2}$, followed by a post exposure bake on a hot plate for three minutes and six minutes at 65° C. and 95° C., respectively. Next, the glass slide was developed in SU8-2000 developer for three minutes and rinsed with isopropyl alcohol to obtain the desired pattern. The glass slide was then hard baked on a hotplate at 150° C. A composition containing 10:1 solvent:PDMS (Sylgard 184, obtained from DowCorning, USA) was poured over the mold and cured at 60° C. to transfer the desired pattern onto the PDMS.

To fabricate the electrodes, a glass slide coated with 10 nm Ti and 100 nm Au was patterned using a positive photoresist, AZ®-P4620 (AZ Electronic Materials, USA). The photoresist was spin coated at 3900 rpm, soft baked at 100° C. for one minute, 150° C. for 1.5 min and then again at 100° C. for one minute. The resist was exposed under UV light with an exposure dose of 288 mJ cm$^{-2}$ and developed for three minutes in AZ400K developer. The glass slide was then hard baked at 100° C. for one hour. Next, the Au layer was etched in a KI:I$_2$ complex (obtained from Transene Company, Inc., USA) for 15 seconds. Finally, the Ti layer was etched in a mixture of 20:1:1 H$_2$O:HF:H$_2$O$_2$ for five seconds. The device 12 was completed by bonding the PDMS layer and the electrode slide by activation of the surfaces under air plasma for 35 seconds at 100 W (using a Harrick PDC-32 G plasma device).

2.2: Testing

Before testing, the MS3110 chip was characterized. It was found that it could measure capacitances as low as 0.1 fF and its dynamic response time was approximately 70 µs. For the following experiments, K was 5.13, and feedback capacitance $C_F$ was selected to make a tradeoff between sensitivity and noise level. $C_F$ was set to 1.197 pF or 1.502 pF. Sampling was performed at 60 Hz and 200 Hz.

Aluminum abrasive particles (diameters 20 µm±10 µm, obtained from Atlantic Equipment Engineers, Inc) were used to test the device 12. To ensure that no particle blocked the 40 µm high microchannel, particles greater than 25 µm were filtered by a 25 µm filter mesh (obtained from Sefar Filtration Inc., USA). Thus, aluminum particles of size varying from 10 µm to 25 µm were used to test the microfluidic device 12. Aluminum particles mixed with the SAE-5W30 lubricant oil were loaded into the inlet reservoir using a syringe and forced to flow through the microchannel by pressure.

Figure 20:
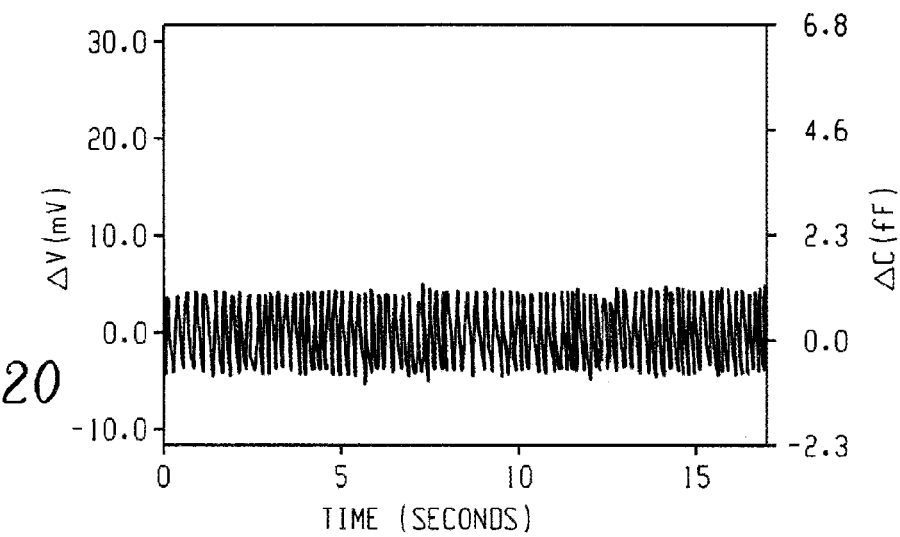
FIG. 20 is a plot of measured capacitance change over time for a lubricant oil without aluminum particles in the microfluidic device of FIGS. 2 and 3 at 60 kHz sampling.
Figure 21:
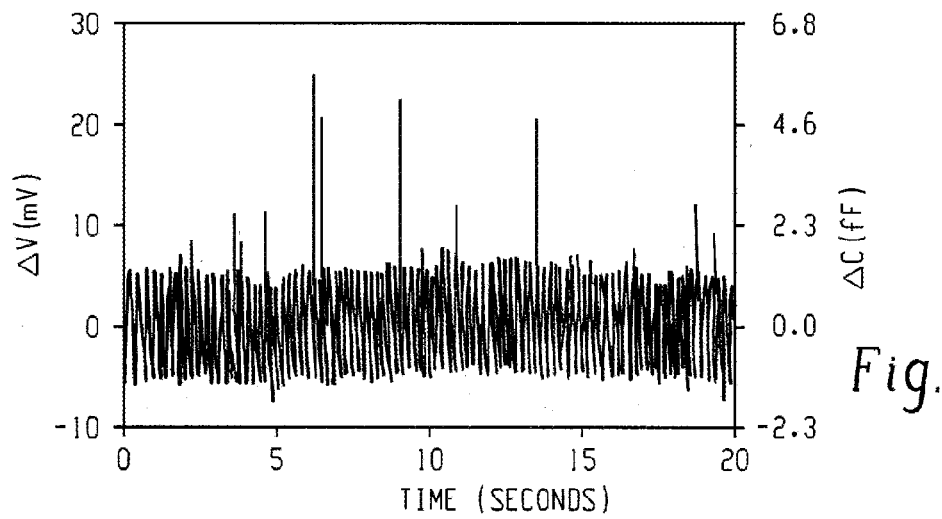
FIG. 21 is a plot of measured capacitance change over time for a lubricant oil containing aluminum wear particles in the microfluidic device of FIGS. 2 and 3 at 60 kHz sampling.
Figure 22:
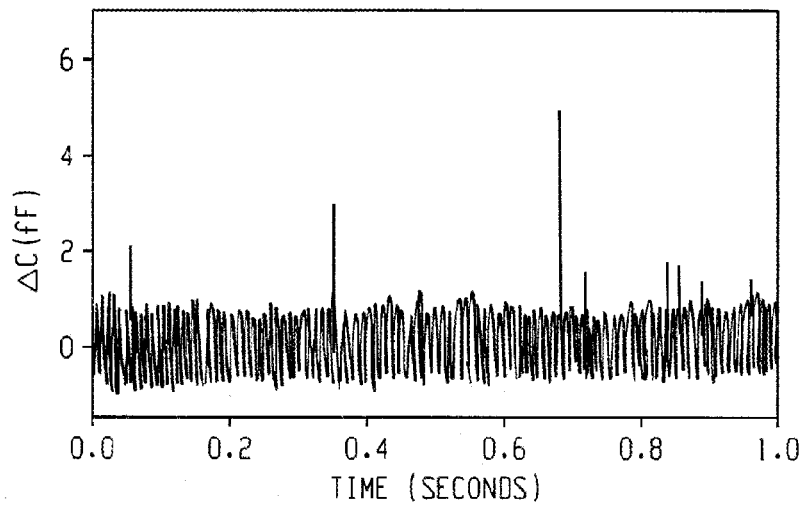
FIG. 22 is a plot of measured capacitance change over time for the lubricant oil containing aluminum wear particles in the microfluidic device of FIGS. 2 and 3 at 200 kHz sampling.

Oil with and without aluminum particles was pumped from inlet reservoir to outlet reservoir using the syringe. The response of the device 12 was recorded. Experimental results are shown in FIGS. 20-22. For FIGS. 20 and 21, measurements were taken at 60 kHz. FIG. 20 shows the response of the device when oil without particles was loaded. No change in capacitance was observed (i.e., nothing substantially above a background variation of about ±1 femtofarads). FIG. 21 shows that when oil with aluminum particles was loaded, capacitive pulses were observed. Each pulse represents the passage of one aluminum particle through the microchannel 34. The magnitude of the pulses was in the range of about 3 to 8 femtofarads. FIG. 22 shows results corresponding to FIG. 21, but with a higher sampling (20 kHz).

Figure 23:
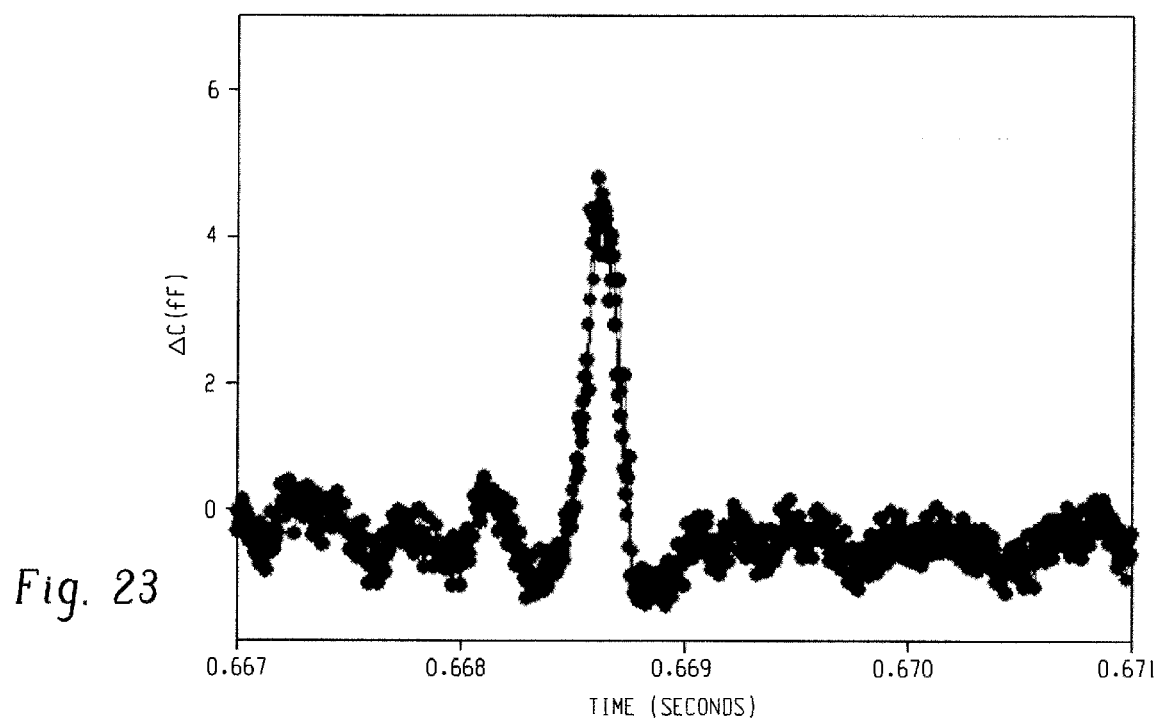
FIG. 23 is a magnified plot of a capacitative pulse representative of a particle passing through the microchannel of the embodiment of FIGS. 2 and 3.

Due to the high viscosity of the oil, a high driving pressure was required to maintain flow in the channel 34, resulting in high particle velocity through the channel. The flow rate was estimated to be about 70 µl/min. This leads to a narrow pulse width (about 0.5 ms). In order to observe the exact shape of an individual pulse, the experiment was repeated using a higher sampling frequency of 200 kHz. The feedback capacitance used in the experiment was $C_F$=1.502 pF. FIG. 23 is a magnified view of a single capacitive pulse due to the passage of an aluminum particle through the microfluidic channel sampled by the DAQ at 200 kHz using $C_F$ set to 1.502 pF. This pulse width is approximately 0.5 ms.

It was noted that many of the aluminum particles settled at the bottom of the inlet reservoir, so that only a small fraction of the particles passed through the microchannel. Analysis of the device 12 using a finite element simulation of the electric fields indicated that the variation of the capacitance change is due primarily to the size variation of the particles. The off-axis passage of the particles through the microchannel also contributes to the variation.

Due to the high viscosity of the oil, a high driving pressure was required to maintain flow in the channel, resulting in high particle velocity through the channel. The device response to 20 µm polystyrene particles (obtained from Sigma Aldrich) suspended in lubrication oil was also tested. No pulses were measured. This is presumably because polystyrene's relative permittivity ($\in_r \approx 2.56$) is similar to that of the lubrication oil ($\in_r \approx 2.3$).

Example 3

Meso-Sized Inductive Sensing Device-Static Testing

To demonstrate the inductive Coulter counting principle, steel particles and aluminum particles were tested in a mesoscale device. The sensor 12 consists of a channel 6.254 mm in diameter filled with SAE 5W-30 motor oil, with a solenoid with 20 turns of 0.254 mm diameter copper wire wound around it, as illustrated in FIG. 5. The solenoid can be modeled as the equivalent circuit shown in FIG. 9, and was measured on an Agilent E4980A precision LCR meter to have $R_s$=0.15Ω and $L_s$=2.44 µH, with parasitic capacitance $C_p$=10.82 pF.

Figure 24:
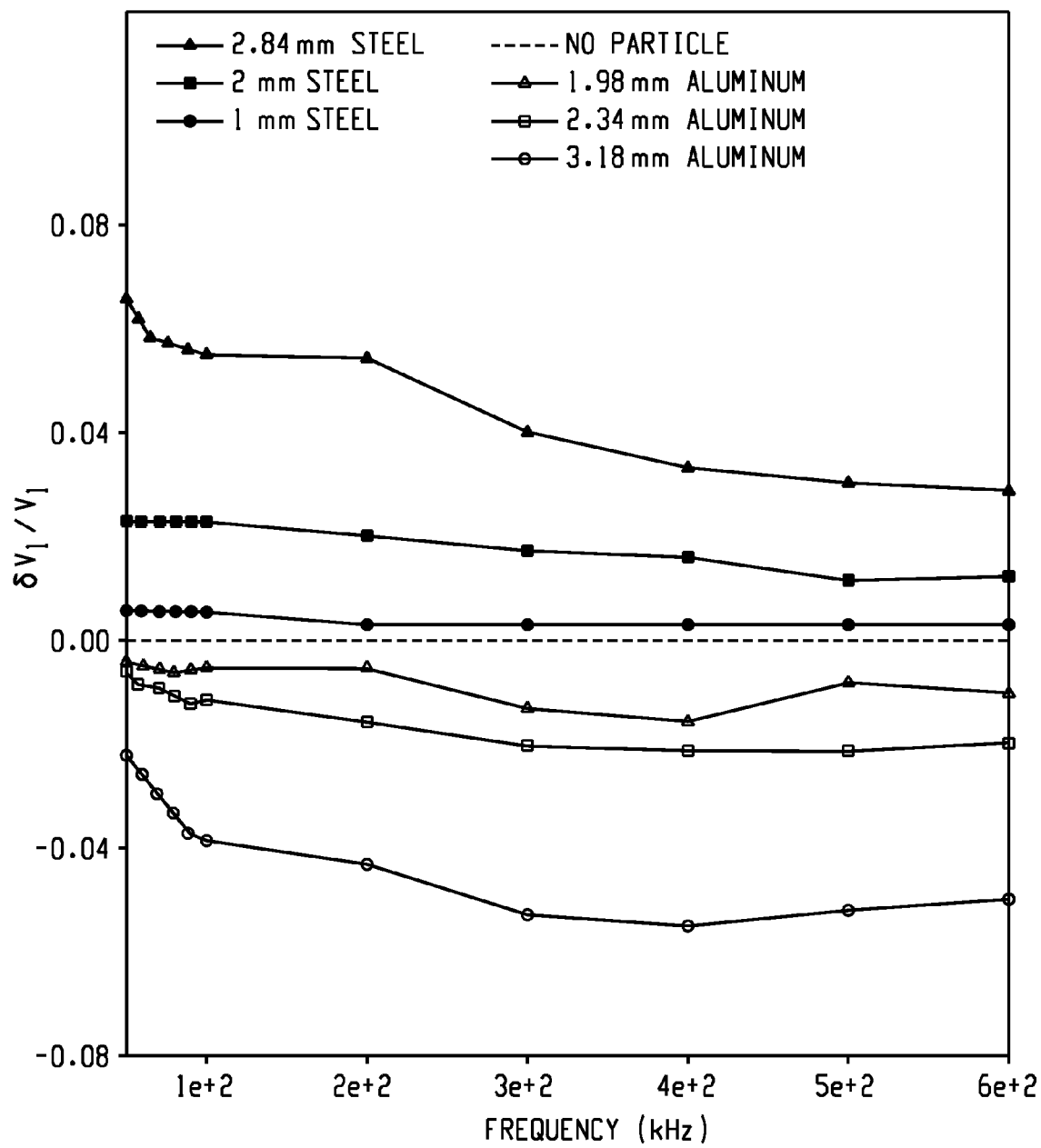
FIG. 24 illustrates static testing results for chromium steel and aluminum particles in an inductive meso-fluidic device.

First, static testing was conducted. Three ferrous and conductive chromium steel N52100 particles (from McMaster-Carr, $\mu_r$=50 with diameters 1 mm, 2 mm and 2.84 mm) and three nonferrous and conductive aluminum alloy 2017 particles (from McMaster-Carr, with diameters 1.98 mm, 2.34 mm, and 3.18 mm) were used. A particle was placed in the center of the channel. A sine wave generator 202 was set to produce a 1 $V_{pp}$ excitation under open-circuit conditions. The generator was connected to the solenoid 200, and the frequency was swept from 100 kHz to 600 kHz. The output voltage $V_1$ was measured using a NI 6251 DAQ system, and the RMS value, calculated in LabVIEW, was used to calculate the relative change in inductance of the solenoid. The results are shown in FIG. 24. In the shown frequency range, the ferrous particles cause a positive change in $L_s$, while the nonferrous particles cause a negative change; larger particles generated larger changes in L.

Example 4

Meso-Sized Inductive Sensing Device-Dynamic Testing

Figure 25:
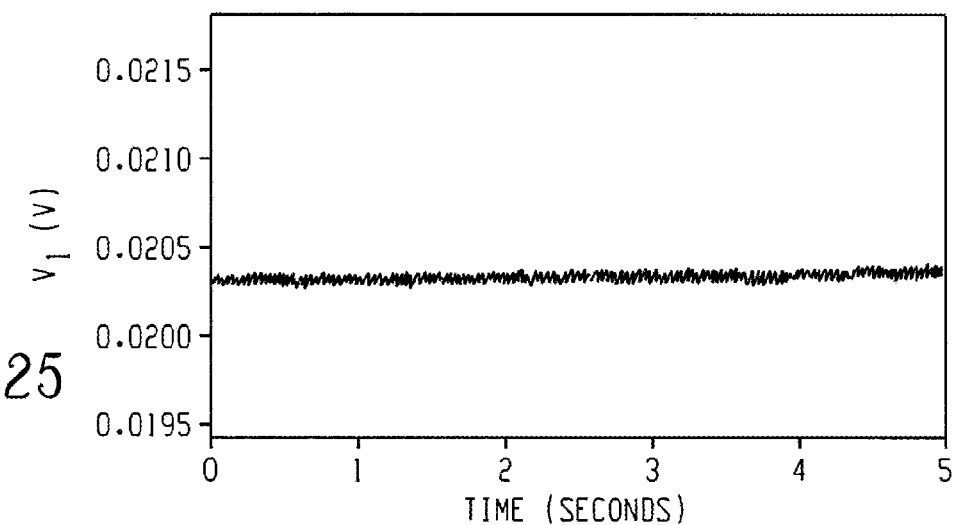
FIGS. 25-27 are plots illustrating dynamic testing results for a 1 Vpp 100 kHz sine wave excitation.
Figure 26:
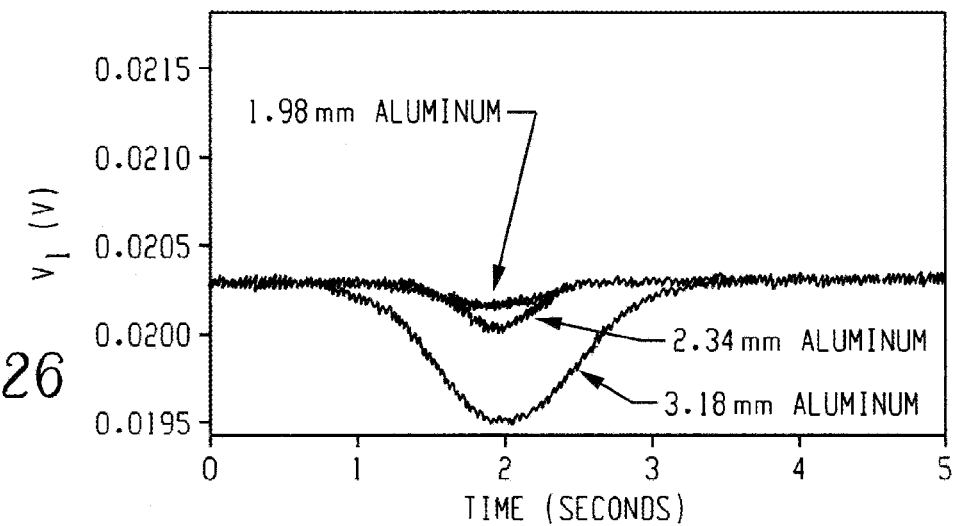
Figure 27:
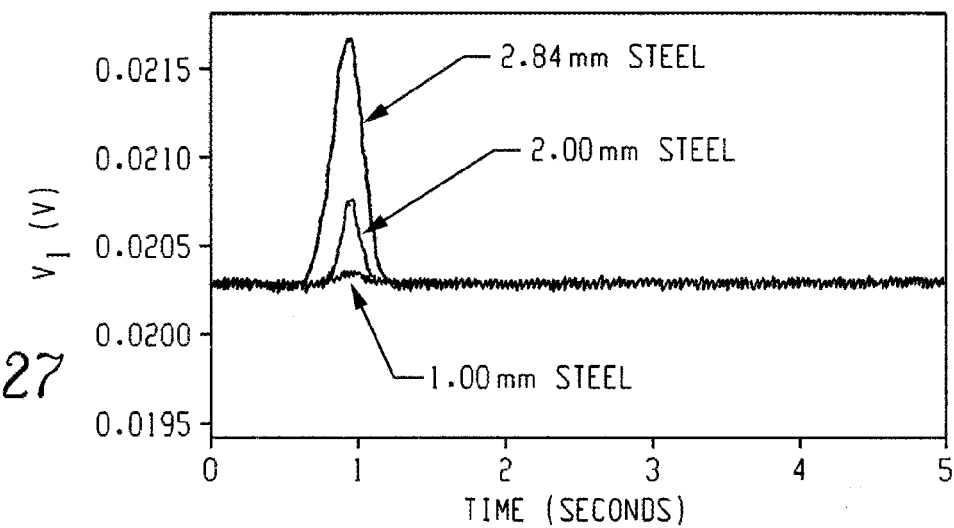

Next, dynamic testing was conducted with the device of Example 3. A fixed excitation frequency of 100 kHz was chosen, as good sensitivity was seen at this frequency for the static test. To mimic operation of a Coulter counter, particles were dropped from the top of the channel and allowed to fall through the channel. The measured waveforms for the RMS values of $V_1$ are shown in FIGS. 25-27. FIG. 25 shows the baseline noise when there was no particle in the lubrication oil. As shown in FIG. 26, the chromium steel particles generated positive pulses, while the aluminum particles generated negative pulses, as shown in FIG. 27. The pulse magnitude was related to the particle size. The results indicate that the inductive Coulter counting device is able to distinguish the two types of particles and evaluate their sizes.

Example 5

Micro-Scale Inductive Sensing Device

A micro-scale device with a sensor as illustrated in FIGS. 6-8 was fabricated. The planar coil of a PL3225TTE4R7M thin film inductor chip (KOA SPEER Electronics, Inc.) was used as the solenoid 200, after using sandpaper to remove the protective covering of the coil. The planar coil was fabricated on a ferrite substrate 38. The 13-turn copper coil was connected to a pair of connection pads 214, 216. Each coil turn has a line width of 43 μm. When a metal particle moved close to the top surface of the planar coil, an inductance change was observed because of the changes in magnetic permeability and eddy current. A ferrous particle caused a positive change in inductance while an aluminum particle caused a negative change of inductance.

Figure 28:
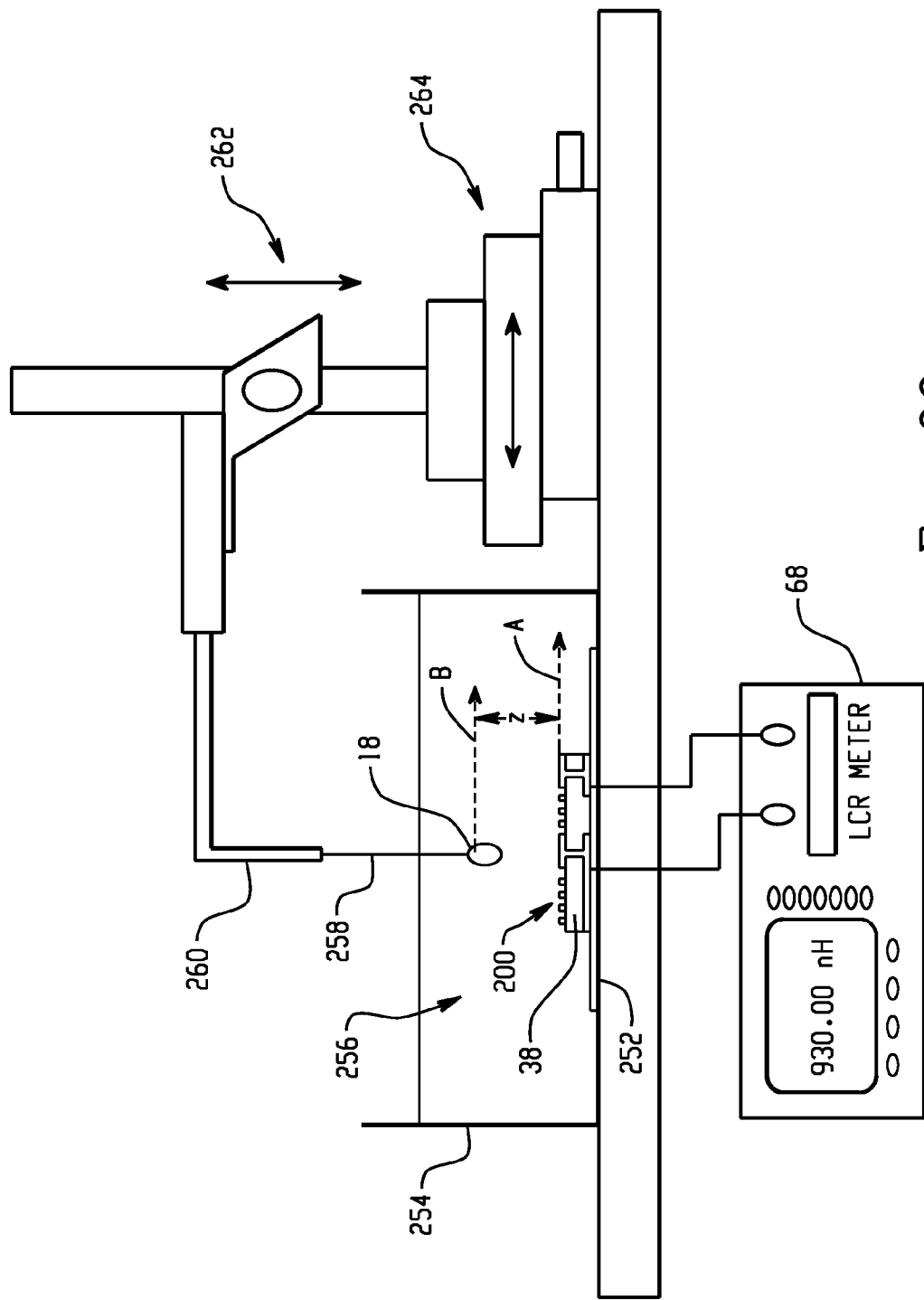
FIG. 28 illustrates a test apparatus for inductive testing.

FIG. 28 illustrates the testing arrangement. There was no microchannel in the testing arrangement. Rather, the microscale planar coil 200 on its substrate 38 was simply affixed to a glass slide 252 using double-sided copper tape (not shown). A strip of 50 μm thick single-sided cellophane tape (not shown) was used to cover the top of the planar coil. This served as both electrical insulation and a protection layer. The microscale sensing assembly was immersed in a petri dish 254 filled with SAE 5W-30 lubrication oil 256. Pseudo-dynamic testing was conducted to demonstrate the sensing using this microscale sensing assembly. Metal particles 18 were fixed at the free end of a glass fiber 258 attached to a mechanical holder 260. The glass fiber was chosen because testing showed that the fiber by itself caused negligible inductance change in the planar coil. Two precision stages 262, 264 were used to control the position of the particle 18. The first stage 262 controlled the vertical distance z between the particle and the planar coil. The second precision stage 264 was used to move the holder and thus the particle in discrete steps across the face of the coil 200. This served to mimic particles passing over the planar coil surface in fluid flow through a microchannel.

For the first test, the distance z of the particle from the face of the planar coil was fixed at z=50 μm; i.e., the particle was in direct contact with the cellophane tape. Measurements were taken at steps of 200 μm horizontally across the face of the coil along line A (z=50 μm) and line B (z~500 μm) indicated in FIG. 24, above the center line of the coil (along the x axis). Because the coil is not perfectly symmetric, the magnetic field produced by the coil is also not symmetric. Thus moving along different lines in the x-y plane produced differently shaped inductance pulses. This particular line of movement was chosen because it resulted in an inductance pulse with a well defined single peak. An Agilent E4980A precision LCR meter 68 was connected to the connection pads of the planar coil to monitor the inductance change. In all tests, the testing signal used for the LCR meter was a 1Vpp, 2 MHz sine wave.

Preliminary impedance measurements indicated that for the planar coil, the capacitance has a relatively insignificant effect on the overall impedance at 2 MHz. Therefore, the LCR meter was set up to assume that the coil consists of a pure inductance and a pure resistance in series, and the inductance reading that it reported was taken as the inductance of the planar coil. The measurement time was set to "short time"; for this setup, the response time of the inductance measurement was 5.8 milliseconds. When there was no metal particle in the lubrication oil, the base inductance measured was 930 nH.

Five metal particles (three iron particles and two aluminum particles) were used in testing. Their approximate sizes are shown in Table 1. The 100 μm and 500 μm aluminum and iron particles were roughly cylindrical in shape. They were created by cutting small lengths of thin metal wires. The 80 μm iron particle was irregular in shape. It was made by filing an iron piece and its maximum dimension was 80 μm as measured with a microscope.

TABLE 1

Metal particles used in testing a micro-fluidic inductive counting device

| Iron particles | Aluminum particles |
| --- | --- |
| 100 μm (D), 100 μm (L) | 100 μm (D), 100 μm (L) |
| 500 μm (D), 500 μm (L) | 500 μm (D), 500 μm (L) |
| 80 μm (D), irregular shape | |

D: Diameter;
L: Length

Figure 29:
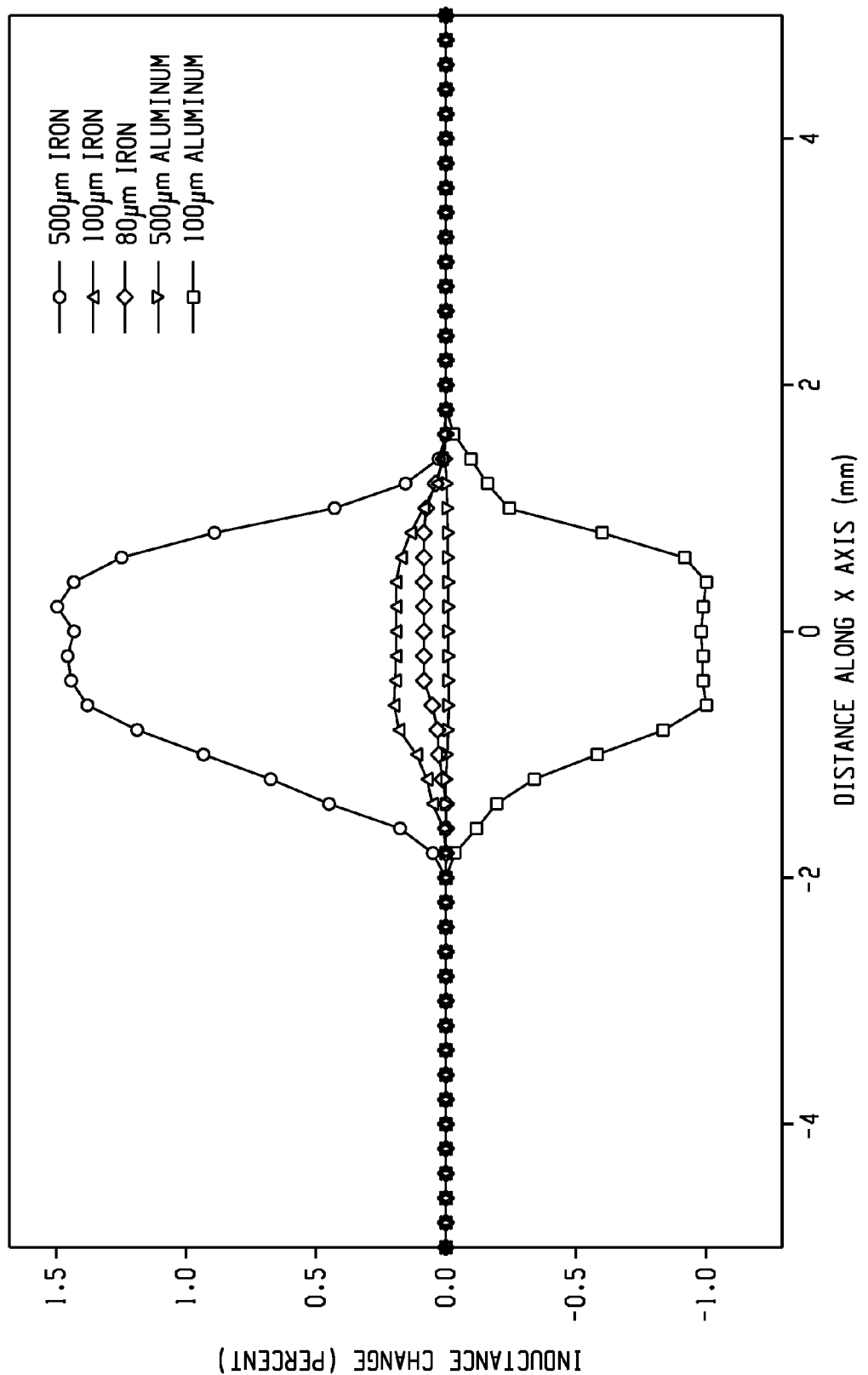
FIG. 29 shows plots of measured relative inductance changes caused by iron and aluminum particles using the test apparatus of FIG. 28.
Figure 30:
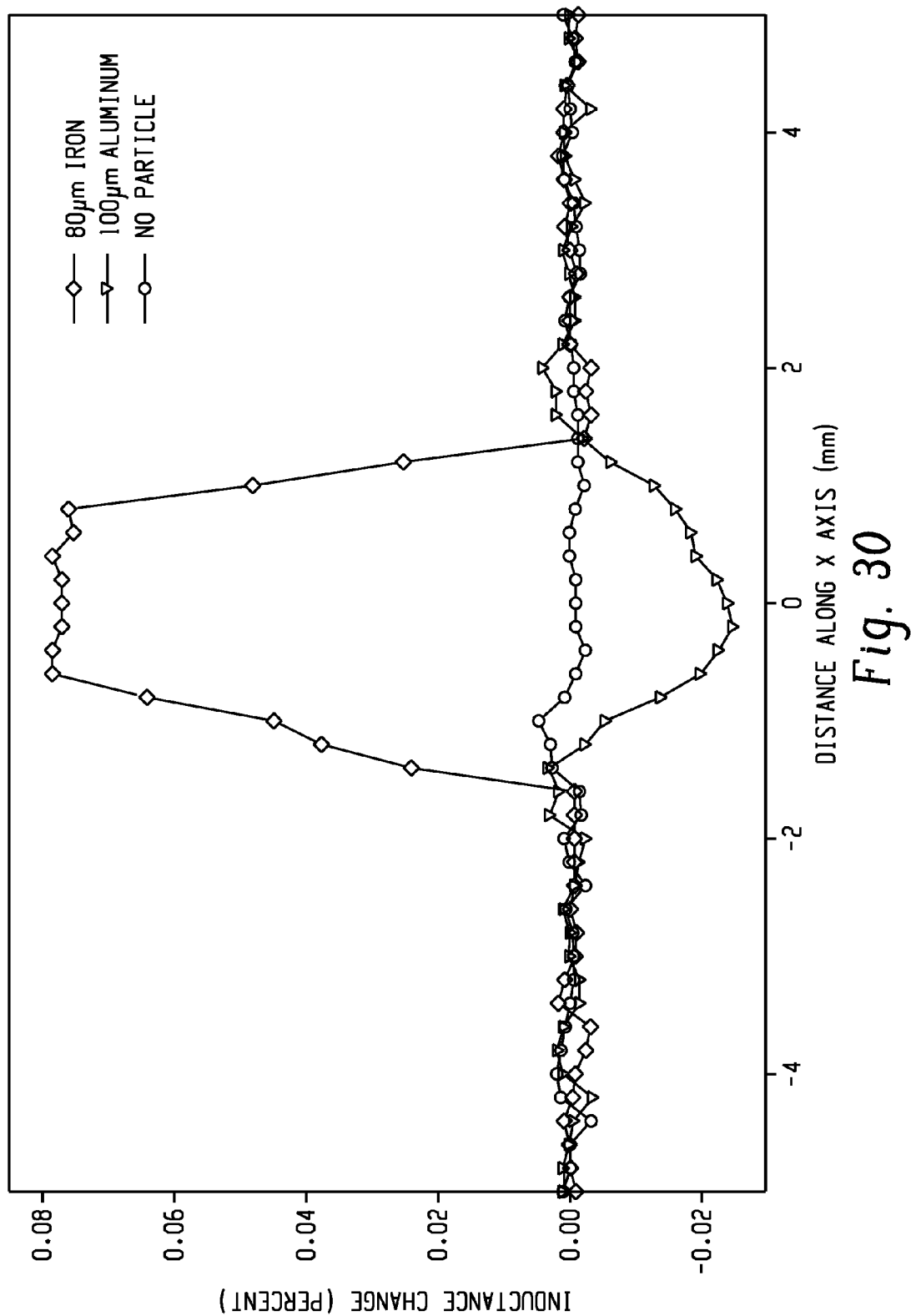
FIG. 30 shows measured relative inductance change caused by a 100 µm aluminum particle and a 80 µm iron particle.

For the first test, the three iron particles and two aluminum particles were used. FIG. 29 shows the inductance pulse caused by all five particles as they were moved along the x-direction. FIG. 30, which is on a different vertical scale than FIG. 29, shows the inductance pulse caused by an 80 μm iron particle and a 100 μm aluminum particle as they were moved along the x-direction, compared to the baseline inductance when no particle was present in the oil. The iron particles caused positive pulses in inductance because the increase in permeability is dominant; the aluminum particles induced negative pulses owing to the eddy current effect. The pulse width is comparable to the width of the planar coil chip, which is 3.2 mm. The pulse heights caused by the 500 μm, 100 μm and 80 μm iron particles correspond to inductance changes of 1.5%, 0.2% and 0.08%, respectively. The pulse heights caused by the 500 μm and 100 μm aluminum particles correspond to inductance changes of −1.0% and −0.025%, respectively. All inductance changes were detectable.

The test results indicate that the planar coil 200 can be used to detect and differentiate ferrous and nonferrous micro-scale particles as small as 80 μm, with a pulse height for a given material that is related to particle size. The results also indicate that by using smaller micro-scale planar coils with denser coil turns fabricated by micromachining, even smaller metal debris particles can be measured and differentiated.

Figure 31:
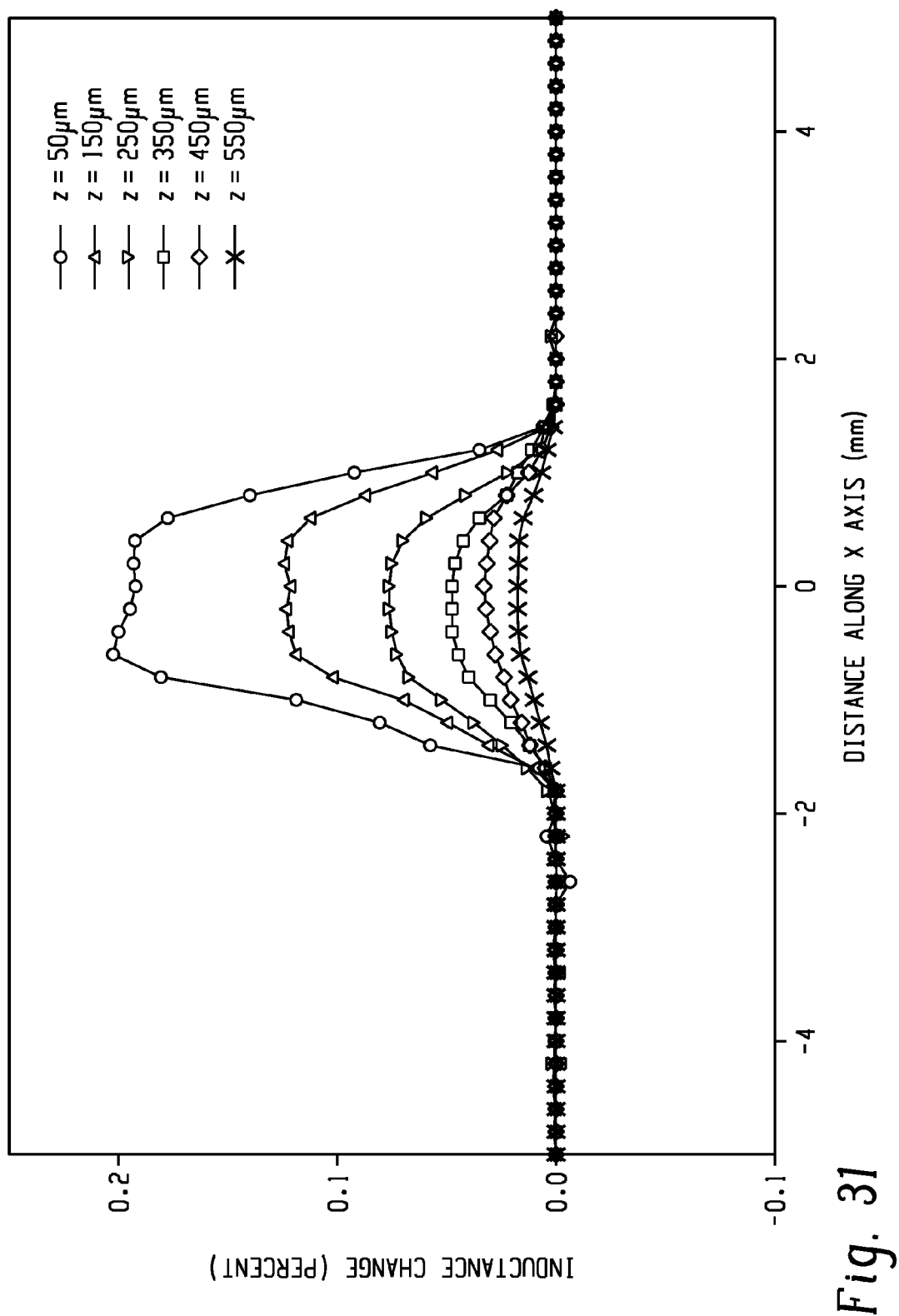
FIG. 31 shows measured relative inductance change caused by a 100 µm iron particle at different vertical distances z from the coil.

A further test was conducted to study the influence of the vertical spacing between the particle and the planar coil on the measured inductance pulse. The 100 μm iron particle was used for this experiment. The particle was initially in direct contact with the cellophane tape (z=50 μm). The distance along the z axis was increased in steps of 100 μm. The results are shown in FIG. 31. The plot shows that as the distance increases from 100 μm to 550 μm, the pulse height reduces from 0.20% to 0.02%. This is because the magnetic field strength drops as z increases; therefore inductance change caused by both the magnetic permeability and eddy current is reduced as well.

Figure 32:
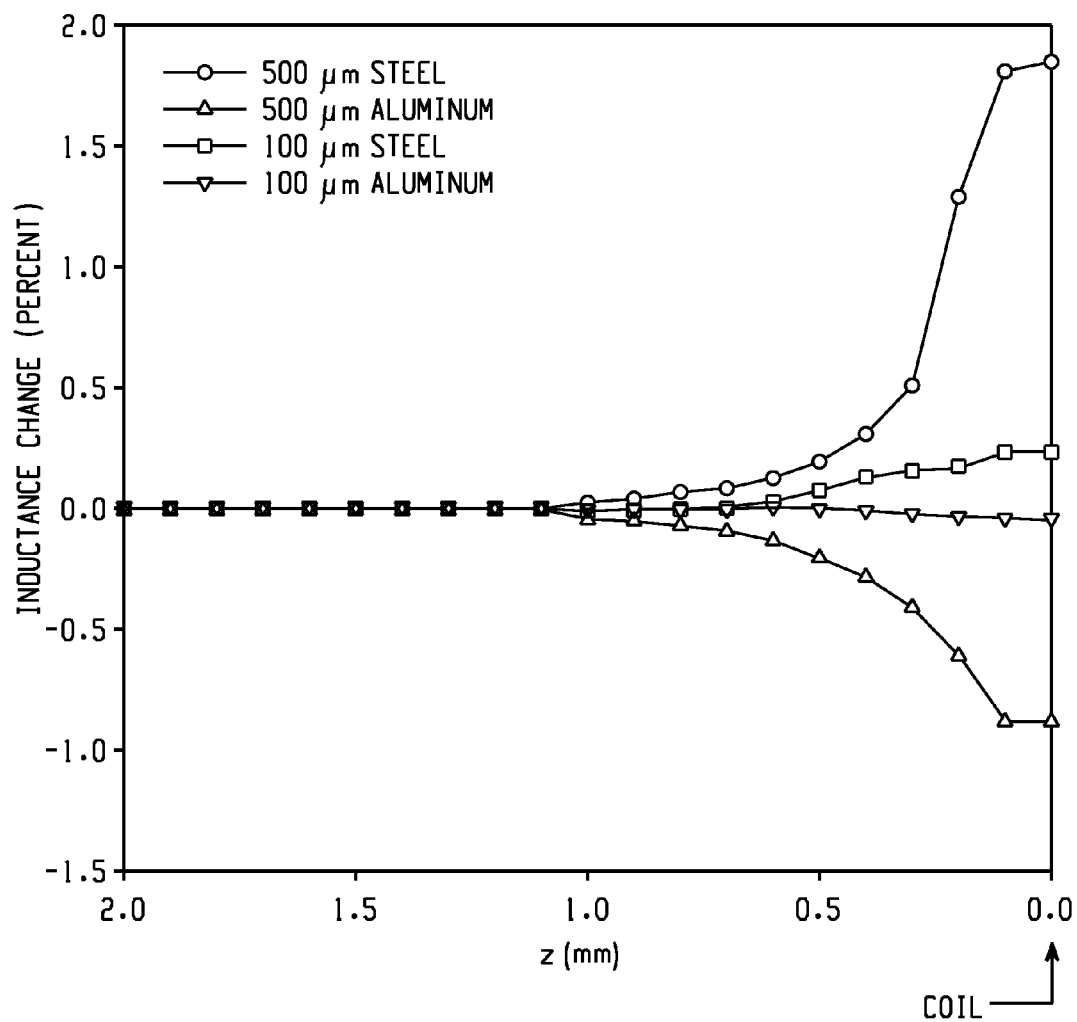
FIG. 32 shows measured relative inductance change caused by a particles traveling in a vertical direction.

To mimic particles passing through the planar coil's center in fluid flow through a microchannel, metal particles fixed at the free end of a glass fiber were moved toward the center of the coil along the z direction. The glass by itself caused negligible inductance change in the planar coil. FIG. 32 shows the measured relative inductance change (representing half an inductive pulse that would be seen in the device of FIG. 14) caused as four different metal particles travel along the z direction. Measurements were taken at 2 MHz using an LCR meter. The result indicates that a microscale planar coil is able to detect and differentiate ferrous and non-ferrous microscale particles as small as 100 μm, with a pulse height that is related to particle size. With smaller microscale planar coils fabricated by micromachining, even smaller metal debris particles could, of course, be measured and differentiated.

As will be appreciated, by controlling the height of the channel in an actual microchannel device 12 to slightly greater than the largest particle to pass through it, such variations can be minimized. Alternatively, a stage to focus particles along a particular line of movement in the channel, at a well controlled vertical distance from the coil may be employed.

Preliminary testing using ferrous and nonferrous particles has demonstrated the feasibility of a microscale device for detection, counting and differentiation of microscale metal particles in nonconductive lubrication oil. Differentiation between ferrous and nonferrous particles can be achieved by monitoring the inductance change of a planar coil. Unlike a bulk measurement method, the developed method produces output pulses with amplitudes correlated with the sizes of individual particles. The sensitivity can be improved by using smaller planar coils with denser coil turns. Thus, this device is suitable for online detection of wear debris in lubrication oil for rotating and reciprocating machinery health monitoring.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. An apparatus for detection of wear particles in a lubricant comprising: a microfluidic device comprising: a microchannel sized for a lubricant containing wear particles to pass therethrough, and at least one coiled electrode in the microchannel; and a detection system for detection of a wear particle passing through the microchannel based on a change in an electrical property of the at least one coiled electrode as a wear particle passes the coiled electrode.

2. The apparatus of claim 1, wherein the wear particles comprise a non-ferrous metal.

3. The apparatus of claim 1, wherein at least some of the wear particles are predominantly formed from non-ferrous metal.

4. The apparatus of claim 1, wherein the lubricant comprises a motor oil.

5. The apparatus of claim 1, wherein the microchannel is sized to allow scanning of individual particles one at a time.

6. The apparatus of claim 5, wherein the microchannel has a minimum dimension that is no more than three times the size of a largest particle to be detected.

7. The apparatus of claim 1, wherein the microchannel has a minimum dimension, measured perpendicular to a direction of flow of the lubricant, of at least 20 μm.

8. The apparatus of claim 1, wherein the microchannel has a minimum dimension, measured perpendicular to the direction of flow of the lubricant, of no greater than 200 μm.

9. The apparatus of claim 1, wherein the electrical property is capacitance.

10. The apparatus of claim 1, wherein the electrical property is inductance.

11. The apparatus of claim 1, wherein the microchannel passes through a hole in a substrate which supports the coiled electrode.

12. The apparatus of claim 1, wherein turns of the coiled electrode are spaced by a distance of less than 50 μm.

13. The apparatus of claim 1, further comprising a first reservoir at a first end of the microchannel and a second reservoir at a second end of the microchannel, the first and second reservoirs each having a minimum dimension greater than a minimum dimension of the microchannel.

14. The apparatus of claim 13, wherein the first reservoir is fluidly connected with an associated lubricated device for receiving the lubricant therefrom.

15. The apparatus of claim 13, wherein the second reservoir is fluidly connected with the associated lubricated device for returning the lubricant thereto.

16. The apparatus of claim 1, wherein the detection system includes a detector which detects changes in an electrical property.

17. The apparatus of claim 16, wherein the detector is capable of detecting capacitance changes of less than 10 femtoFarads or inductance changes of less than 0.1 nanoHenry.

18. The apparatus of claim 1, wherein the detection system includes an analyzer which analyses the detected changes in the electrical property and determines at least one of a size of a wear particle passing through the microchannel and a number of wear particles passing through the microchannel in a selected time interval.

19. The apparatus of claim 1, wherein the detection system includes a signaling device which provides a visual or audible signal in response to a detection of wear particles which exceed at least one of a threshold size and a threshold number in a selected time interval.

20. The apparatus of claim 1, further comprising a filter for filtering the lubricant of large particles prior to passing through the microchannel.

21. The apparatus of claim 1, wherein the microchannel comprises a plurality of microchannels, each with a respective at least one coiled electrode.

22. A system for detection of wear particles comprising the apparatus of claim 1 and a lubricated device fluidly coupled with the microfluidic device which supplies lubricant containing wear particles to the microfluidic device.

23. A method for detection of wear particles in a lubricant comprising supplying a lubricant to the microfluidic device of claim 1 and detecting a change in the electrical property with the detection system.

24. A method for detection of wear particles in a lubricant comprising: supplying a lubricant containing wear particles to a microchannel; monitoring changes in an electrical property as wear particles pass at least one coiled electrode positioned in the microchannel; and detecting wear particles passing through the microchannel based on the monitored change in the electrical property.

25. The method of claim 24, wherein the supplying comprises fluidly coupling the microchannel with a lubricated device whereby lubricant passes between the lubricated device and the microchannel.

26. The method of claim 24, wherein the monitoring comprises detecting pulses which exceed a threshold capacitance or inductance change.

27. A method for forming an apparatus for detection of wear particles in a lubricant comprising: providing a coiled electrode on a substrate; mounting a body to the substrate such that a microchannel is defined between the substrate and the body over the coiled electrode, such that the coiled electrode is in the microchannel; coupling the ends of the coiled electrode with a detection system capable of detecting a change in capacitance or inductance generated when a lubricant containing a wear particle passes through the microchannel; wherein the detection system can differentiate between ferrous and non-ferrous particles.

* * * * *